(12) United States Patent
Makower et al.

(10) Patent No.: US 9,039,680 B2
(45) Date of Patent: *May 26, 2015

(54) IMPLANTABLE DEVICES AND METHODS FOR DELIVERING DRUGS AND OTHER SUBSTANCES TO TREAT SINUSITIS AND OTHER DISORDERS

(75) Inventors: Joshua Makower, Los Altos, CA (US); John Y. Chang, Mountain View, CA (US); Julia D. Vrany, Sunnyvale, CA (US); Amrish Jayprakash Walke, Mountain View, CA (US)

(73) Assignee: Acclarent, Inc., Menlo Park, CA (US)

( * ) Notice: Subject to any disclaimer, the term of this patent is extended or adjusted under 35 U.S.C. 154(b) by 384 days.

This patent is subject to a terminal disclaimer.

(21) Appl. No.: 12/107,005

(22) Filed: Apr. 21, 2008

(65) Prior Publication Data
US 2009/0005763 A1    Jan. 1, 2009

Related U.S. Application Data

(62) Division of application No. 10/912,578, filed on Aug. 4, 2004, now Pat. No. 7,361,168.

(51) Int. Cl.
*A61M 29/00*      (2006.01)
*A61M 31/00*      (2006.01)
(Continued)

(52) U.S. Cl.
CPC ............... *A61M 31/002* (2013.01); *A61B 5/06* (2013.01); *A61B 5/064* (2013.01); *A61B 5/411* (2013.01); *A61B 17/24* (2013.01); *A61B 17/320725* (2013.01); *A61B 17/320758* (2013.01);
(Continued)

(58) Field of Classification Search
USPC ........... 604/500, 506, 514, 516, 890.1, 891.1, 604/93.01; 606/196; 128/204.12, 898; 424/434
See application file for complete search history.

(56) References Cited

U.S. PATENT DOCUMENTS

| 446,173 | A | 2/1891 | Hancock |
| 504,424 | A | 9/1893 | De Pezzer |

(Continued)

FOREIGN PATENT DOCUMENTS

| CA | 2563711 | 10/2006 |
| CH | 668188 | 12/1988 |

(Continued)

OTHER PUBLICATIONS

Chien, Y.W et al., Nasal Systemic Drug Delivery, Drugs and the pharmaceutical sciences, vol. 39, pp. 60-63.
(Continued)

*Primary Examiner* — Matthew F Desanto
*Assistant Examiner* — Matthew A Engel

(57) ABSTRACT

Implantable devices and methods for delivering drugs and other substances to locations within the body of a human or animal subject to treat or diagnose sinusitis and a variety of other disorders. The invention includes implantable substance delivery devices that comprise reservoirs and barriers that control the rate at which substances pass out of the reservoirs. The delivery devices may be advanced into the body using guidewires, catheters, ports, introducers and other access apparatus. In some embodiments the delivery devices may be loaded with one or more desired substance before their introduction into the body. In other embodiments the delivery devices are loaded and/or reloaded with a desired substance after the delivery device has been introduced into the body.

33 Claims, 12 Drawing Sheets

(51) Int. Cl.
*A61B 5/06* (2006.01)
*A61B 5/00* (2006.01)
*A61B 17/24* (2006.01)
*A61M 25/10* (2013.01)
*A61B 17/3207* (2006.01)
*A61B 17/34* (2006.01)
*A61B 19/00* (2006.01)
*A61B 17/22* (2006.01)
*A61F 2/18* (2006.01)
*A61F 2/82* (2013.01)
*A61M 25/00* (2006.01)

(52) U.S. Cl.
CPC ..... *A61B17/320783* (2013.01); *A61B 17/3478* (2013.01); *A61B 19/5244* (2013.01); *A61B 2017/22061* (2013.01); *A61F 2/18* (2013.01); *A61F 2/82* (2013.01); *A61F 2250/0039* (2013.01); *A61M 25/0029* (2013.01); *A61M 25/007* (2013.01); *A61M 25/10* (2013.01); *A61M 2025/0037* (2013.01); *A61M 2025/1052* (2013.01)

(56) References Cited

U.S. PATENT DOCUMENTS

| | | | |
|---|---|---|---|
| 513,667 A | 1/1894 | Buckingham |
| 705,346 A | 7/1902 | Hamilton |
| 798,775 A | 9/1905 | Forsyth |
| 816,792 A | 4/1906 | Green et al. |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,911,671 A | 5/1933 | Blanvell |
| 2,201,749 A | 5/1940 | Vandegrift |
| 2,525,183 A | 3/1947 | Robison |
| 2,493,326 A | 1/1950 | Trinder |
| 2,691,985 A | 10/1954 | Newsom |
| 2,847,997 A | 8/1958 | Tibone |
| 2,899,227 A | 8/1959 | Gschwend |
| 2,906,179 A | 9/1959 | Bower |
| 2,995,832 A | 8/1961 | Alderson |
| 3,009,265 A | 11/1961 | Bezark |
| 3,037,286 A | 6/1962 | Bower |
| 3,173,418 A | 3/1965 | Baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow et al. |
| 3,731,963 A | 5/1973 | Pond |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita et al. |
| 3,834,394 A | 9/1974 | Hunter et al. |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |

(56) References Cited

U.S. PATENT DOCUMENTS

| | | | |
|---|---|---|---|
| 4,917,419 A | 4/1990 | Mora, Jr. et al. | |
| 4,917,667 A | 4/1990 | Jackson | |
| 4,919,112 A | 4/1990 | Siegmund | |
| 4,920,967 A | 5/1990 | Cottonaro et al. | |
| 4,925,445 A | 5/1990 | Sakamoto et al. | |
| 4,940,062 A | 7/1990 | Hampton et al. | |
| 4,943,275 A | 7/1990 | Stricker | |
| 4,946,466 A | 8/1990 | Pinchuk et al. | |
| 4,961,433 A | 10/1990 | Christian | |
| 4,966,163 A | 10/1990 | Kraus et al. | |
| 4,984,581 A | 1/1991 | Stice | |
| 4,994,033 A | 2/1991 | Shockey et al. | |
| 4,998,916 A | 3/1991 | Hammerslag et al. | |
| 4,998,917 A | 3/1991 | Gaiser et al. | |
| 5,001,825 A | 3/1991 | Halpern | |
| 5,002,322 A | 3/1991 | Fukumoto | |
| 5,019,075 A | 5/1991 | Spears et al. | |
| 5,019,372 A | 5/1991 | Folkman et al. | |
| 5,020,514 A | 6/1991 | Heckele | |
| 5,021,043 A | 6/1991 | Becker et al. | |
| 5,024,650 A | 6/1991 | Hagiwara et al. | |
| 5,024,658 A | 6/1991 | Kozlov et al. | |
| 5,026,384 A | 6/1991 | Farr et al. | |
| 5,030,227 A | 7/1991 | Rosenbluth et al. | |
| 5,041,089 A | 8/1991 | Mueller et al. | |
| 5,044,678 A | 9/1991 | Detweiler | |
| 5,053,007 A | 10/1991 | Euteneuer | |
| 5,055,051 A | 10/1991 | Duncan | |
| 5,060,660 A | 10/1991 | Gambale et al. | |
| 5,067,489 A | 11/1991 | Lind | |
| 5,069,226 A | 12/1991 | Yamauchi et al. | |
| 5,087,244 A | 2/1992 | Wolinsky et al. | |
| 5,087,246 A | 2/1992 | Smith | |
| 5,090,595 A | 2/1992 | Vandoninck | |
| 5,090,910 A | 2/1992 | Narlo | |
| 5,112,228 A | 5/1992 | Zouras | |
| 5,116,311 A | 5/1992 | Lofstedt | |
| 5,127,393 A | 7/1992 | McFarlin et al. | |
| 5,137,517 A | 8/1992 | Loney et al. | |
| 5,139,510 A | 8/1992 | Goldsmith, III et al. | |
| 5,139,832 A | 8/1992 | Hayashi et al. | |
| D329,496 S | 9/1992 | Wotton | |
| 5,152,747 A | 10/1992 | Olivier | |
| 5,163,989 A | 11/1992 | Campbell et al. | |
| 5,167,220 A | 12/1992 | Brown | |
| 5,168,864 A | 12/1992 | Shockey | |
| 5,169,043 A | 12/1992 | Catania | |
| 5,169,386 A | 12/1992 | Becker et al. | |
| 5,171,233 A | 12/1992 | Amplatz et al. | |
| 5,180,368 A | 1/1993 | Garrison | |
| 5,183,470 A | 2/1993 | Wettermann | |
| 5,189,110 A | 2/1993 | Ikematu et al. | |
| 5,195,168 A | 3/1993 | Yong | |
| 5,197,457 A | 3/1993 | Adair | |
| 5,207,695 A | 5/1993 | Trout, III | |
| 5,211,952 A | 5/1993 | Spicer et al. | |
| 5,215,105 A | 6/1993 | Kizelshteyn et al. | |
| 5,221,260 A | 6/1993 | Burns et al. | |
| 5,226,302 A | 7/1993 | Anderson | |
| 5,230,348 A | 7/1993 | Ishibe et al. | |
| 5,236,422 A | 8/1993 | Eplett, Jr. | |
| 5,243,996 A | 9/1993 | Hall | |
| D340,111 S | 10/1993 | Yoshikawa | |
| 5,250,059 A | 10/1993 | Andreas et al. | |
| 5,251,092 A | 10/1993 | Brady et al. | |
| 5,252,183 A | 10/1993 | Shaban et al. | |
| 5,255,679 A | 10/1993 | Imran | |
| 5,263,926 A | 11/1993 | Wilk | |
| 5,264,260 A | 11/1993 | Saab | |
| 5,267,965 A | 12/1993 | Deniega | |
| 5,270,086 A | 12/1993 | Hamlin | |
| 5,273,052 A | 12/1993 | Kraus et al. | |
| 5,275,593 A | 1/1994 | Easley et al. | |
| 5,286,254 A | 2/1994 | Shapland et al. | |
| 5,295,694 A | 3/1994 | Levin | |
| 5,295,959 A | 3/1994 | Gurbel et al. | |
| 5,300,085 A | 4/1994 | Yock | |
| 5,304,123 A | 4/1994 | Atala et al. | |
| 5,308,326 A | 5/1994 | Zimmon | |
| 5,313,967 A | 5/1994 | Lieber et al. | |
| 5,314,417 A | 5/1994 | Stephens et al. | |
| 5,315,618 A | 5/1994 | Yoshida | |
| 5,333,620 A | 8/1994 | Moutafis et al. | |
| 5,334,167 A | 8/1994 | Cocanower | |
| 5,336,163 A | 8/1994 | DeMane et al. | |
| 5,341,818 A | 8/1994 | Abrams et al. | |
| 5,342,296 A | 8/1994 | Persson et al. | |
| 5,343,865 A | 9/1994 | Gardineer et al. | |
| 5,345,945 A | 9/1994 | Hodgson et al. | |
| 5,346,075 A | 9/1994 | Nichols et al. | |
| 5,346,508 A | 9/1994 | Hastings | |
| 5,348,537 A | 9/1994 | Wiesner et al. | |
| 5,350,396 A | 9/1994 | Eliachar | |
| 5,352,199 A | 10/1994 | Tower | |
| 5,356,418 A | 10/1994 | Shturman | |
| 5,368,049 A | 11/1994 | Raman et al. | |
| 5,368,566 A | 11/1994 | Crocker | |
| 5,372,138 A | 12/1994 | Crowley et al. | |
| 5,372,584 A | 12/1994 | Zink et al. | |
| D355,031 S | 1/1995 | Yoshikawa | |
| 5,386,817 A | 2/1995 | Jones | |
| 5,391,147 A | 2/1995 | Imran et al. | |
| 5,391,179 A | 2/1995 | Mezzoli | |
| 5,402,799 A | 4/1995 | Colon et al. | |
| 5,409,444 A | 4/1995 | Kensey et al. | |
| 5,411,475 A * | 5/1995 | Atala et al. | 604/96.01 |
| 5,411,476 A | 5/1995 | Abrams et al. | |
| 5,411,477 A | 5/1995 | Saab | |
| 5,415,633 A | 5/1995 | Lazarus | |
| 5,425,370 A | 6/1995 | Vilkomerson | |
| 5,439,446 A | 8/1995 | Barry | |
| 5,441,494 A | 8/1995 | Ortiz | |
| 5,441,497 A | 8/1995 | Narciso, Jr. | |
| 5,450,853 A | 9/1995 | Hastings et al. | |
| 5,451,221 A | 9/1995 | Cho et al. | |
| 5,454,817 A | 10/1995 | Katz | |
| 5,458,572 A | 10/1995 | Campbell et al. | |
| 5,465,717 A | 11/1995 | Imran et al. | |
| 5,465,733 A | 11/1995 | Hinohara et al. | |
| 5,478,565 A | 12/1995 | Geria | |
| 5,486,181 A | 1/1996 | Cohen et al. | |
| 5,496,338 A | 3/1996 | Miyagi et al. | |
| 5,497,783 A | 3/1996 | Urick et al. | |
| 5,507,301 A | 4/1996 | Wasicek et al. | |
| 5,507,725 A | 4/1996 | Savage et al. | |
| 5,507,766 A | 4/1996 | Kugo et al. | |
| 5,512,055 A | 4/1996 | Domb et al. | |
| 5,514,128 A | 5/1996 | Hillsman et al. | |
| 5,519,532 A | 5/1996 | Broome | |
| 5,531,676 A | 7/1996 | Edwards et al. | |
| 5,533,985 A | 7/1996 | Wang | |
| 5,538,008 A | 7/1996 | Crowe | |
| 5,546,964 A | 8/1996 | Stangerup | |
| 5,549,542 A | 8/1996 | Kovalcheck | |
| 5,558,073 A | 9/1996 | Pomeranz et al. | |
| 5,558,652 A | 9/1996 | Henke | |
| 5,562,619 A | 10/1996 | Mirarchi et al. | |
| 5,568,809 A | 10/1996 | Ben-haim | |
| 5,578,007 A | 11/1996 | Imran | |
| 5,578,048 A | 11/1996 | Pasqualucci et al. | |
| 5,584,827 A | 12/1996 | Korteweg et al. | |
| 5,591,194 A | 1/1997 | Berthiaume | |
| 5,599,284 A | 2/1997 | Shea | |
| 5,599,304 A | 2/1997 | Shaari | |
| 5,599,576 A | 2/1997 | Opolski | |
| 5,601,087 A | 2/1997 | Gunderson et al. | |
| 5,601,594 A | 2/1997 | Best | |
| 5,607,386 A | 3/1997 | Flam | |
| 5,617,870 A | 4/1997 | Hastings et al. | |
| 5,626,374 A | 5/1997 | Kim | |
| 5,633,000 A | 5/1997 | Grossman et al. | |
| 5,634,908 A | 6/1997 | Loomas | |
| 5,638,819 A | 6/1997 | Manwaring et al. | |
| 5,643,251 A | 7/1997 | Hillsman et al. | |

(56) References Cited

U.S. PATENT DOCUMENTS

| | | |
|---|---|---|
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,389 A | 1/1998 | Louw et al. |
| 5,708,175 A | 1/1998 | Koyanagi et al. |
| 5,711,315 A | 1/1998 | Jerusalmy |
| 5,713,839 A | 2/1998 | Shea |
| 5,713,855 A * | 2/1998 | Shippert .................. 604/516 |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,824,044 A | 10/1998 | Quiachon et al. |
| 5,824,048 A | 10/1998 | Tuch |
| 5,824,173 A | 10/1998 | Fontirroche et al. |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Sahatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,976,573 A * | 11/1999 | Kim .......................... 424/489 |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,997,562 A | 12/1999 | Zadno-Azizi |
| 6,006,126 A | 12/1999 | Cosman |
| 6,006,130 A | 12/1999 | Higo et al. |
| 6,007,516 A | 12/1999 | Burbank |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | Becker |
| 6,122,541 A | 9/2000 | Cosman et al. |
| 6,123,697 A | 9/2000 | Shippert |
| 6,136,006 A | 10/2000 | Johnson et al. |
| 6,139,510 A | 10/2000 | Palermo |
| 6,142,957 A | 11/2000 | Diamond et al. |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedelmayer |
| 6,249,180 B1 | 6/2001 | Maalej et al. |
| 6,254,550 B1 | 7/2001 | McNamara et al. |

(56) References Cited

U.S. PATENT DOCUMENTS

| | | |
|---|---|---|
| 6,268,574 B1 | 7/2001 | Edens |
| 6,293,957 B1 | 9/2001 | Peters et al. |
| 6,297,227 B1 | 10/2001 | Johnson |
| 6,302,875 B1 | 10/2001 | Makower et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,332,089 B1 | 12/2001 | Acker et al. |
| 6,332,891 B1 | 12/2001 | Himes |
| 6,340,360 B1 | 1/2002 | Lyles et al. |
| 6,344,028 B1 * | 2/2002 | Barry ................... 604/96.01 |
| 6,348,041 B1 | 2/2002 | Klint |
| 6,352,503 B1 | 3/2002 | Matsui et al. |
| 6,375,615 B1 | 4/2002 | Flaherty et al. |
| 6,375,629 B1 | 4/2002 | Muni et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,423,012 B1 | 7/2002 | Kato et al. |
| 6,425,877 B1 | 7/2002 | Edwards |
| 6,432,986 B2 | 8/2002 | Levin |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,511,418 B2 | 1/2003 | Shahidi et al. |
| 6,514,249 B1 | 2/2003 | Maguire et al. |
| 6,517,478 B2 | 2/2003 | Khadem |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 * | 4/2003 | Lavigne ................... 128/207.18 |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,794 B2 | 7/2003 | Shimoda et al. |
| 6,596,009 B1 | 7/2003 | Jelic |
| 6,607,546 B1 | 8/2003 | Murken |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,652,472 B2 | 11/2003 | Jafari et al. |
| 6,652,480 B1 | 11/2003 | Imran et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,755,812 B2 | 6/2004 | Peterson et al. |
| 6,776,772 B1 | 8/2004 | Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,817,976 B2 | 11/2004 | Rovegno |
| 6,832,715 B2 | 12/2004 | Eungard et al. |
| D501,677 S | 2/2005 | Becker |
| 6,851,290 B1 | 2/2005 | Meier et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,927,478 B2 | 8/2005 | Paek |
| 6,939,361 B1 | 9/2005 | Kleshinski |
| 6,955,657 B1 | 10/2005 | Webler |
| 6,966,906 B2 | 11/2005 | Brown |
| 6,979,290 B2 | 12/2005 | Mourlas et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,011,654 B2 | 3/2006 | Dubrul et al. |
| 7,022,105 B1 | 4/2006 | Edwards |
| 7,043,961 B2 | 5/2006 | Pandey et al. |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,706 B2 | 9/2006 | Hogle |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,294,345 B2 | 11/2007 | Haapakumpu et al. |
| 7,294,365 B2 | 11/2007 | Hayakawa et al. |
| 7,316,168 B2 | 1/2008 | van der Knokke et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,361,168 B2 * | 4/2008 | Makower et al. ............. 604/509 |
| 7,366,562 B2 | 4/2008 | Dukesherer |
| 7,371,210 B2 | 5/2008 | Brock et al. |

(56) References Cited

U.S. PATENT DOCUMENTS

| | | | |
|---|---|---|---|
| 7,381,205 B2 | 6/2008 | Thommen | |
| 7,410,480 B2 * | 8/2008 | Muni et al. | 604/509 |
| 7,419,497 B2 * | 9/2008 | Muni et al. | 606/196 |
| 7,442,191 B2 | 10/2008 | Hovda et al. | |
| 7,452,351 B2 | 11/2008 | Miller et al. | |
| 7,454,244 B2 | 11/2008 | Kassab et al. | |
| 7,462,175 B2 | 12/2008 | Chang et al. | |
| D586,465 S | 2/2009 | Faulkner et al. | |
| D586,916 S | 2/2009 | Faulkner et al. | |
| 7,488,313 B2 | 2/2009 | Segal et al. | |
| 7,493,156 B2 | 2/2009 | Manning et al. | |
| 7,500,971 B2 | 3/2009 | Chang et al. | |
| D590,502 S | 4/2009 | Geisser et al. | |
| 7,520,876 B2 | 4/2009 | Ressemann et al. | |
| 7,532,920 B1 | 5/2009 | Ainsworth et al. | |
| 7,559,925 B2 | 7/2009 | Goldfarb et al. | |
| 7,625,335 B2 | 12/2009 | Deichmann et al. | |
| 7,641,668 B2 | 1/2010 | Perry et al. | |
| 7,645,272 B2 | 1/2010 | Chang et al. | |
| 7,648,367 B1 | 1/2010 | Makower et al. | |
| 7,654,997 B2 | 2/2010 | Makower et al. | |
| 7,717,933 B2 | 5/2010 | Becker | |
| 7,736,301 B1 | 6/2010 | Webler et al. | |
| 7,740,642 B2 | 6/2010 | Becker | |
| 7,753,929 B2 | 7/2010 | Becker | |
| 7,799,048 B2 | 9/2010 | Hudson et al. | |
| 7,837,672 B2 | 11/2010 | Intoccia | |
| D630,321 S | 1/2011 | Hamilton, Jr. | |
| D632,791 S | 2/2011 | Murner | |
| 7,988,705 B2 | 8/2011 | Galdonik et al. | |
| 8,439,687 B1 | 5/2013 | Morriss et al. | |
| 2001/0016684 A1 | 8/2001 | Shahidi | |
| 2001/0023332 A1 | 9/2001 | Hahnen | |
| 2001/0027307 A1 | 10/2001 | Dubrul et al. | |
| 2001/0029317 A1 | 10/2001 | Hayakawa | |
| 2001/0034530 A1 | 10/2001 | Malackowski et al. | |
| 2001/0051761 A1 | 12/2001 | Khadem | |
| 2002/0002349 A1 | 1/2002 | Flaherty et al. | |
| 2002/0006961 A1 | 1/2002 | Katz et al. | |
| 2002/0010384 A1 | 1/2002 | Shahidi et al. | |
| 2002/0010426 A1 | 1/2002 | Clayman et al. | |
| 2002/0016564 A1 | 2/2002 | Courtney et al. | |
| 2002/0026155 A1 | 2/2002 | Mangosong | |
| 2002/0029030 A1 | 3/2002 | Lurie et al. | |
| 2002/0031941 A1 | 3/2002 | Cote et al. | |
| 2002/0055746 A1 | 5/2002 | Burke et al. | |
| 2002/0062133 A1 | 5/2002 | Gilson et al. | |
| 2002/0077852 A1 | 6/2002 | Ford et al. | |
| 2002/0082558 A1 | 6/2002 | Samson et al. | |
| 2002/0082583 A1 | 6/2002 | Lerner | |
| 2002/0090388 A1 * | 7/2002 | Humes et al. | 424/422 |
| 2002/0103459 A1 | 8/2002 | Sparks et al. | |
| 2002/0107475 A1 | 8/2002 | Maginot | |
| 2002/0116043 A1 | 8/2002 | Garibaldi et al. | |
| 2002/0165521 A1 | 11/2002 | Cioanta et al. | |
| 2003/0013985 A1 | 1/2003 | Saadat | |
| 2003/0014036 A1 | 1/2003 | Varner et al. | |
| 2003/0017111 A1 | 1/2003 | Rabito | |
| 2003/0032942 A1 | 2/2003 | Theeuwes et al. | |
| 2003/0040697 A1 | 2/2003 | Pass et al. | |
| 2003/0069521 A1 | 4/2003 | Reynolds et al. | |
| 2003/0069549 A1 | 4/2003 | MacMahon et al. | |
| 2003/0073955 A1 | 4/2003 | Otawara | |
| 2003/0073972 A1 * | 4/2003 | Rosenman et al. | 604/502 |
| 2003/0083608 A1 | 5/2003 | Evans et al. | |
| 2003/0083613 A1 | 5/2003 | Schaer | |
| 2003/0100886 A1 | 5/2003 | Segal et al. | |
| 2003/0109810 A1 | 6/2003 | Brennan et al. | |
| 2003/0114732 A1 | 6/2003 | Webler et al. | |
| 2003/0120339 A1 | 6/2003 | Banik et al. | |
| 2003/0130598 A1 | 7/2003 | Manning et al. | |
| 2003/0163154 A1 | 8/2003 | Miyata et al. | |
| 2003/0164952 A1 | 9/2003 | Deichmann et al. | |
| 2003/0171650 A1 | 9/2003 | Tartaglia et al. | |
| 2003/0181827 A1 | 9/2003 | Hojeibane et al. | |
| 2003/0185872 A1 | 10/2003 | Kochinke | |
| 2003/0208194 A1 | 11/2003 | Hovda et al. | |
| 2003/0209096 A1 | 11/2003 | Pandey et al. | |
| 2003/0225329 A1 | 12/2003 | Rossner et al. | |
| 2004/0015150 A1 | 1/2004 | Zadno-Azizi | |
| 2004/0018980 A1 | 1/2004 | Gurney et al. | |
| 2004/0034311 A1 | 2/2004 | Mihalcik | |
| 2004/0043052 A1 | 3/2004 | Hunter et al. | |
| 2004/0058992 A1 | 3/2004 | Marinello et al. | |
| 2004/0064083 A1 | 4/2004 | Becker | |
| 2004/0064105 A1 | 4/2004 | Capes et al. | |
| 2004/0064150 A1 * | 4/2004 | Becker | 606/196 |
| 2004/0097788 A1 | 5/2004 | Mourlas et al. | |
| 2004/0098017 A1 | 5/2004 | Saab et al. | |
| 2004/0116958 A1 | 6/2004 | Gopferich et al. | |
| 2004/0122471 A1 | 6/2004 | Toby et al. | |
| 2004/0127820 A1 | 7/2004 | Clayman et al. | |
| 2004/0158229 A1 | 8/2004 | Quinn | |
| 2004/0167440 A1 | 8/2004 | Sharrow | |
| 2004/0167442 A1 | 8/2004 | Shireman et al. | |
| 2004/0167443 A1 | 8/2004 | Shireman et al. | |
| 2004/0181175 A1 | 9/2004 | Clayman et al. | |
| 2004/0193073 A1 | 9/2004 | DeMello et al. | |
| 2004/0193139 A1 | 9/2004 | Armstrong et al. | |
| 2004/0230095 A1 | 11/2004 | Stefanchik et al. | |
| 2004/0230131 A1 | 11/2004 | Kassab et al. | |
| 2004/0230156 A1 | 11/2004 | Schreck et al. | |
| 2004/0236231 A1 | 11/2004 | Knighton et al. | |
| 2004/0249243 A1 | 12/2004 | Kleiner | |
| 2004/0249267 A1 | 12/2004 | Gilboa | |
| 2004/0254625 A1 * | 12/2004 | Stephens et al. | 623/1.1 |
| 2004/0267347 A1 | 12/2004 | Cervantes | |
| 2005/0027249 A1 | 2/2005 | Reifart et al. | |
| 2005/0043706 A1 | 2/2005 | Eaton et al. | |
| 2005/0049486 A1 | 3/2005 | Urquhart et al. | |
| 2005/0055077 A1 | 3/2005 | Marco et al. | |
| 2005/0059931 A1 | 3/2005 | Garrison et al. | |
| 2005/0089670 A1 | 4/2005 | Large et al. | |
| 2005/0107720 A1 | 5/2005 | Burmeister et al. | |
| 2005/0107738 A1 | 5/2005 | Slater et al. | |
| 2005/0113687 A1 | 5/2005 | Herweck et al. | |
| 2005/0113850 A1 | 5/2005 | Tagge | |
| 2005/0119590 A1 | 6/2005 | Burmeister et al. | |
| 2005/0124856 A1 | 6/2005 | Fujikura et al. | |
| 2005/0131316 A1 | 6/2005 | Flagle et al. | |
| 2005/0143687 A1 | 6/2005 | Rosenblatt et al. | |
| 2005/0182319 A1 | 8/2005 | Glossop | |
| 2005/0228260 A1 | 10/2005 | Burwell et al. | |
| 2005/0228412 A1 | 10/2005 | Surti | |
| 2005/0234507 A1 | 10/2005 | Geske et al. | |
| 2005/0240147 A1 | 10/2005 | Makower et al. | |
| 2005/0244472 A1 | 11/2005 | Hughes et al. | |
| 2005/0245906 A1 | 11/2005 | Makower et al. | |
| 2005/0283221 A1 | 12/2005 | Mann et al. | |
| 2005/0288549 A1 | 12/2005 | Mathis | |
| 2005/0288759 A1 | 12/2005 | Jones et al. | |
| 2006/0004286 A1 | 1/2006 | Chang et al. | |
| 2006/0004323 A1 | 1/2006 | Chang et al. | |
| 2006/0063973 A1 | 3/2006 | Makower et al. | |
| 2006/0067982 A1 | 3/2006 | Haapakumpu et al. | |
| 2006/0074318 A1 | 4/2006 | Ahmed et al. | |
| 2006/0085027 A1 | 4/2006 | Santin et al. | |
| 2006/0095066 A1 | 5/2006 | Chang et al. | |
| 2006/0106361 A1 | 5/2006 | Muni et al. | |
| 2006/0107957 A1 | 5/2006 | Djupesland | |
| 2006/0116749 A1 | 6/2006 | Willink et al. | |
| 2006/0149310 A1 | 7/2006 | Becker | |
| 2006/0173291 A1 | 8/2006 | Glossop | |
| 2006/0173382 A1 | 8/2006 | Schreiner | |
| 2006/0190022 A1 | 8/2006 | Beyar et al. | |
| 2006/0210605 A1 | 9/2006 | Chang et al. | |
| 2006/0211752 A1 | 9/2006 | Kohn et al. | |
| 2006/0271024 A1 | 11/2006 | Gertner et al. | |
| 2007/0005094 A1 | 1/2007 | Eaton et al. | |
| 2007/0020196 A1 | 1/2007 | Pipkin et al. | |
| 2007/0049929 A1 | 3/2007 | Catanese, III et al. | |
| 2007/0073269 A1 | 3/2007 | Becker | |
| 2007/0112358 A1 | 5/2007 | Abbott | |
| 2007/0129751 A1 | 6/2007 | Muni et al. | |

(56) References Cited

U.S. PATENT DOCUMENTS

| | | | |
|---|---|---|---|
| 2007/0135789 A1 | 6/2007 | Chang et al. | |
| 2007/0167682 A1 | 7/2007 | Goldfarb et al. | |
| 2007/0208252 A1 | 9/2007 | Makower | |
| 2007/0208301 A1 | 9/2007 | Evard et al. | |
| 2007/0250105 A1 | 10/2007 | Ressemann et al. | |
| 2007/0269385 A1 | 11/2007 | Yun et al. | |
| 2007/0293727 A1 | 12/2007 | Goldfarb et al. | |
| 2007/0293946 A1 | 12/2007 | Gonzales et al. | |
| 2008/0015540 A1 | 1/2008 | Muni et al. | |
| 2008/0015544 A1 | 1/2008 | Keith et al. | |
| 2008/0033519 A1 | 2/2008 | Burwell et al. | |
| 2008/0051804 A1 | 2/2008 | Cottler et al. | |
| 2008/0082045 A1 | 4/2008 | Goldfarb et al. | |
| 2008/0097154 A1 | 4/2008 | Makower et al. | |
| 2008/0097239 A1 | 4/2008 | Chang et al. | |
| 2008/0097295 A1 | 4/2008 | Makower et al. | |
| 2008/0097400 A1 | 4/2008 | Chang et al. | |
| 2008/0097514 A1 | 4/2008 | Chang et al. | |
| 2008/0097515 A1 | 4/2008 | Chang et al. | |
| 2008/0097516 A1 | 4/2008 | Chang et al. | |
| 2008/0103361 A1 | 5/2008 | Makower et al. | |
| 2008/0103521 A1 | 5/2008 | Makower et al. | |
| 2008/0119693 A1 | 5/2008 | Makower et al. | |
| 2008/0125046 A1 | 5/2008 | Deng et al. | |
| 2008/0125626 A1 | 5/2008 | Chang et al. | |
| 2008/0154250 A1 | 6/2008 | Makower et al. | |
| 2008/0154345 A1 | 6/2008 | Taylor | |
| 2008/0187098 A1 | 8/2008 | Gertner et al. | |
| 2008/0188870 A1 | 8/2008 | Andre et al. | |
| 2008/0195041 A1 | 8/2008 | Goldfarb et al. | |
| 2008/0208242 A1 | 8/2008 | Becker | |
| 2008/0208243 A1 | 8/2008 | Becker | |
| 2008/0215082 A1 | 9/2008 | Becker | |
| 2008/0215083 A1 | 9/2008 | Becker | |
| 2008/0228085 A1 | 9/2008 | Jenkins et al. | |
| 2008/0234720 A1 | 9/2008 | Chang et al. | |
| 2008/0275483 A1 | 11/2008 | Makower et al. | |
| 2008/0281156 A1 | 11/2008 | Makower et al. | |
| 2008/0287908 A1* | 11/2008 | Muni et al. | 604/506 |
| 2008/0319424 A1 | 12/2008 | Muni et al. | |
| 2009/0017090 A1 | 1/2009 | Arensdorf et al. | |
| 2009/0028923 A1 | 1/2009 | Muni et al. | |
| 2009/0030274 A1 | 1/2009 | Goldfarb et al. | |
| 2009/0047326 A1 | 2/2009 | Eaton et al. | |
| 2009/0088728 A1 | 4/2009 | Dollar et al. | |
| 2009/0093823 A1 | 4/2009 | Chang et al. | |
| 2009/0156980 A1 | 6/2009 | Eaton et al. | |
| 2009/0163890 A1 | 6/2009 | Clifford et al. | |
| 2009/0187089 A1 | 7/2009 | Say et al. | |
| 2009/0187098 A1 | 7/2009 | Makower et al. | |
| 2009/0192492 A1 | 7/2009 | Eaton et al. | |
| 2009/0198216 A1* | 8/2009 | Muni et al. | 604/514 |
| 2009/0227945 A1 | 9/2009 | Eaton et al. | |
| 2009/0240112 A1 | 9/2009 | Goldfarb et al. | |
| 2009/0240237 A1 | 9/2009 | Goldfarb et al. | |
| 2009/0312745 A1 | 12/2009 | Goldfarb et al. | |
| 2010/0087811 A1 | 4/2010 | Herrin et al. | |
| 2010/0114066 A1* | 5/2010 | Makower et al. | 604/514 |
| 2010/0121308 A1* | 5/2010 | Muni et al. | 604/514 |
| 2010/0198191 A1 | 8/2010 | Clifford et al. | |
| 2013/0281982 A1 | 10/2013 | Makower et al. | |

FOREIGN PATENT DOCUMENTS

| | | |
|---|---|---|
| CN | 2151720 | 1/1994 |
| CN | 2352818 | 12/1999 |
| DE | 3202878 | 8/1983 |
| DE | 04032096 | 4/1992 |
| DE | 04406077 | 9/1994 |
| DE | 08810044 | 11/1998 |
| DE | 29923582 | 12/2000 |
| DE | 10104663 | 8/2002 |
| DE | 10105592 | 8/2002 |
| EP | 0129634 | 1/1985 |
| EP | 0257605 | 3/1988 |
| EP | 0355996 | 2/1990 |
| EP | 0418391 | 3/1991 |
| EP | 0427852 | 5/1991 |
| EP | 0623582 | 11/1994 |
| EP | 0624349 | 11/1994 |
| EP | 0744400 | 11/1996 |
| EP | 0585757 | 6/1997 |
| EP | 0893426 | 1/1999 |
| EP | 1042998 | 10/2000 |
| EP | 01166710 | 1/2002 |
| EP | 01413258 | 4/2004 |
| FR | 2859377 | 3/2005 |
| FR | 2916144 | 11/2008 |
| GB | 2125874 | 3/1984 |
| GB | 2305174 | 4/1997 |
| JP | 53-067935 | 6/1978 |
| JP | 5367935 | 6/1978 |
| JP | 10-24098 | 1/1989 |
| JP | 3-504935 | 10/1991 |
| JP | 4-221313 | 8/1992 |
| JP | 5-211985 | 8/1993 |
| JP | H06-508278 | 9/1994 |
| JP | 6-277296 | 10/1994 |
| JP | 07-327916 | 12/1995 |
| JP | 8-317989 | 12/1996 |
| JP | 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-062080 | 3/2003 |
| JP | 2003-521327 | 7/2003 |
| JP | 2004-357728 | 12/2004 |
| JP | 2005-532869 | 11/2005 |
| RU | 2213530 | 10/2003 |
| SU | 1662571 | 7/1991 |
| WO | 90/11053 | 10/1990 |
| WO | WO 90/11053 | 10/1990 |
| WO | WO 90/014115 | 11/1990 |
| WO | WO 90/14865 | 12/1990 |
| WO | WO 91/17787 | 11/1991 |
| WO | WO 92/15286 | 9/1992 |
| WO | WO 92/22350 | 12/1992 |
| WO | 94/12095 | 6/1994 |
| WO | WO 96/29071 | 9/1996 |
| WO | 97/24161 | 6/1997 |
| WO | WO 99/24106 | 5/1999 |
| WO | WO 99/30655 | 6/1999 |
| WO | 99/32041 | 7/1999 |
| WO | 00/09192 | 2/2000 |
| WO | 00/23009 | 4/2000 |
| WO | 00/51672 | 9/2000 |
| WO | WO 00/53252 | 9/2000 |
| WO | 01/45572 | 6/2001 |
| WO | WO 01/45572 | 6/2001 |
| WO | 01/56481 | 8/2001 |
| WO | WO 01/54558 | 8/2001 |
| WO | 01/70325 | 9/2001 |
| WO | WO 01/74266 | 10/2001 |
| WO | WO 01/97895 | 12/2001 |
| WO | WO 02/062269 | 8/2002 |
| WO | 03/049603 | 6/2003 |
| WO | 03/063703 | 8/2003 |
| WO | WO 03/105657 | 12/2003 |
| WO | WO 2004/006788 | 1/2004 |
| WO | WO 2004/018980 | 3/2004 |
| WO | 2004/026391 | 4/2004 |
| WO | WO 2004/082525 A2 | 9/2004 |
| WO | WO 2004/082525 A3 | 9/2004 |
| WO | WO 2005/018730 | 3/2005 |
| WO | WO 2005/077450 | 8/2005 |
| WO | WO 2005/089670 | 9/2005 |
| WO | 2005/117755 | 12/2005 |
| WO | 2006/034008 | 3/2006 |

(56) References Cited

FOREIGN PATENT DOCUMENTS

| WO | 2006/078884 | 7/2006 |
|---|---|---|
| WO | WO 2006/107957 | 10/2006 |
| WO | 2006/116597 | 11/2006 |
| WO | 2006/118737 | 11/2006 |
| WO | 2006/135853 | 12/2006 |
| WO | WO 2007/111636 | 10/2007 |
| WO | 2007/124260 | 11/2007 |
| WO | 2008/036149 | 3/2008 |
| WO | 2008/045242 | 4/2008 |
| WO | WO 2008/051918 | 5/2008 |
| WO | 2008/134382 | 11/2008 |

OTHER PUBLICATIONS

Colla, A., et al 'Trihaloacetylated Enol Ethers—General Synthetic Procedure and Heterocyclic Ring Closure Reactions with Hydroxylamine' Synthesis Jun. 1991 pp. 483-486.
Friedman, M. M.D., et al, 'Operative Techniques in Otolarynology—Head and Neck Surgery' vol. 12, No. 2, Jun. 2001, pp. 60-65.
Gerus, I.I. et al β-Ethoxyvinyl Polyfluroroalkyl Ketones—Versatile Synthones in Fluoroorganic Chemistry' Journal of Fluorine Chemistry (1994) pp. 195-198, vol. 69 Elsevier Science S.A.
Gorlov, D.V. et al 'Acylation of 2-Methoxypropene with Anhydrides and Halides of Perflurocarboxylic Acids in the Presence of Tertiary Amines' Russian Chemical Bulletin, Sep. 1999, pp. 1791-1792 vol. 48 No. 9, Kluwer Academic/Plenum Publishers.
Gottman, et al., Balloon dilatation in the nasal cavity and paranasal sinuses; CIRSE, Sep. 25, 2004.
Gottman, et al., Balloon Dilatation of Recurrent Ostial Occlusion of the Front Sinus' ECR, Mar. 2, 2001.
Gottman, et al., Balloon Dilatation of Recurrent Ostial Occlusion of the Front Sinus' OASIS—Online Abstract Submission and Invitation System, 1996-2006, Coe-Truman Technologies, Inc.
Hospital Corpsman Sickcall Screener's Handbook Naval Hospital Great Lakes. http:/ /www.brooksidepress.org/Products/Operationa. Medicine/DATA. 2001 pp. 1-6.
Kuhn, et al., The Agger Nasi Cell in Frontal Recess Obstruction: An Anatomic, Radiology and Clinical Correlation, Operative Techniques in Otolaryngology—Head and Neck Surgery, vol. 2, No. 4, 1991, pp. 226-231.
Single-Pole and Multi-Pole Lightguides for UV Spot Light Curing Systems. http://www.dymax.com/products/curing_equipment/lightguids/light. 2004 pp. 1-2.
International Search Report, PCT International Application No. PCT/US06/02004.
U.S. Appl. No. 10/829,917.
U.S. Appl. No. 10/912,578.
U.S. Appl. No. 10/944,270.
U.S. Appl. No. 11/037,548.
U.S. Appl. No. 11/150,847.
U.S. Appl. No. 11/527,773.
U.S. Appl. No. 11/544,009.
U.S. Appl. No. 11/648,159.
U.S. A..1. No. 11/789,704.
U.S. Appl. No. 11/925,540.
U.S. Appl. No. 11/926,326.
U.S. Appl. No. 11/928,097.
Argon Medical. Maxxim Medical. Ad for Sniper Elite™ Hydrophilic Ni—Ti Alloy Guidewire (2001).
Aust, R., et al 'The Functional Size of the Human Maxillary Ostium in Vivo' Acta. Otolaryn. (1978) vol. 78 pp. 432-435.
Baim, D.S., MD *Grossman's Cardiac Catheterization, Angiography, and Intervention* (2000) Lippincott Williams & Wilkins pp. 76, 84 & 214.
Bartel, N. 'An Improved Stent for Use in the Surgical Management of Congenital Posterior Choanal Atresia' J. Laryngol. Otol. (1988) vol. 102 pp. 146-147.
Becker, A.E. 'Restenosis After Angioplasty' The Lancet (1988) vol. 331, No. 8584 p. 532.
Bellis, M. History of the Catheter—Balloon Catheter—Thomas Fogarty. http://inventors.about.com/library/inventors/blcatheter.htm?p=1 [retrieved on Sep. 20, 2010] Retrieved from the Internet.
Brown, C.L. et al 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Bumm, P., H. Kaiser et al 'Cortizontherapie, Corticoide in Klinik and Praxis' Thieme, Stuggart (1992) pp. 390-401 [Summary of textbook].
Casserly, I.P. et al Chapter 7. 'Guides and Wires in Percutaneous Coronary Intervention' *Strategic Approaches in Coronary Intervention* (2006) Lippincott Williams & Wilkins pp. 91-99.
Cohen et al 'Endoscopic Sinus Surgery: Where we are and where we are going' Current Opinion in Otolaryngology & Head and Neck Surgery (2005) vol. 13 pp. 32-38.
Costa, M.N. et al 'Endoscopic Study of the Intranasal Ostium in External Dacryocystorhinostomy Postoperative. Influence of Saline Solution and 5-Flurorouracil' Clinics. (2007) vol. 62, Issue 1 pp. 41-46. http://www.scielo.br/scielo.php?pid=S1807-59322007000100007&script=sci_arttext.
Cussler, E.L. Diffusion: Mass Transfer in Fluid Systems Cambridge University Press (1996) [Summary of textbook].
Domb, A. et al Handbook of Biodegradable Polymers Harwood Academic Publishers (1997) [Summary of textbook].
Draf, W. 'Endonasal Micro-Endoscopic Frontal Sinus Surgery: the Fulda Concept' Op Tech Otolaryngol Head Neck Surg. (1991) vol. 2 pp. 234-240.
Edmond et al 'ENT Surgical Stimulator' Nov. 1998 Final Report Cooperative Agreement No. DAMD17-95-2-5023.
ENT Checklist; Physical Examination Performance Checklist [date of publication unknown].
Eremychev, V.A. 'Needles for Puncture and Drainage of the Maxillary Sinus' Meditsinskaya Tekhnika, No. 5 (1974) pp. 54-55.
Feldman, R.L. et al 'New Steerable, Ultra-Low-Profile, Fixed Wire Angioplasty Catheter: Initial Experience With the Cordis Orion™ Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg. (1990) vol. 103, No. 1 pp. 135-137.
Friedman et al 'Middle Turbinate Medialization and Preservation in Endoscopic Surgery' Otolaryngol. Head Neck Surg. (2000) vol. 123, No. 1, Part 1. pp. 76-80.
Fung, M.K.T. 'How I Do It—Head and Neck and Plasic Surgery. A Targeted Problem and its Solution. Template for Frontal Osteoplastic Flap' Laryngoscope. (1986) vol. 96 pp. 578-579.
Gatot, A. et al., 'Early Treatment of Orbital Floor Fractures with Catheter Balloon in Children' Int. J. Pediatric Otorhinolaryngol (1991) vol. 21 pp. 97-101.
Gopferich 'Polymer Degradation and Erosion: Mechanisms and Applications' Eur. J. Pharm. Biophar. (1996) vol. 42 pp. 1-11.
Gottman, et al. 'Balloon Dilatation of Recurrent Ostial Occlusion of the Front Sinus' Abstract No. B-04353. European Congress of Radiology. (Mar. 2, 2001).
Gupta, D. et al 'Dacryocystitis Secondary to an Iatrogenic Foreign Body in the Lacrimal Apparatus' Ear, Nose & Throat Journal (2009) http://findarticles.com/p/articles/mi_m0BUM/is_7_88/ai_n32428620/.
Hashim, et al 'Balloon Compression of the Intermaxillary Sinus for Intractable Post Traumatic Bleeding from the Maxillary Artery' Scandinavian Journal of Plastic and Reconstructive Surgery and Hand Surgery (1999) vol. 33 pp. 321-324.
Hopf, J.U.G. et al 'Miniature Endoscopes in Otorhinolaryngologic Applications' Min Invas Ther & Allied Technol. (1998) vol. 7, No. 3 pp. 209-218.
Hosemann, W. et al *A Dissection Course on Endoscopic Endonasal Sinus Surgery* (2005) Endo-Press, Tuttlingen pp. 4-37.
Hosemann, W. et al 'Endonasal Frontal Sinusotomy in Surgical Management of Chronic Sinusitis: A Critical Evaluation' American Journal of Rhinology (1997) vol. 11, No. 1 pp. 1-9.
Hosemann, M.E. et al 'Experimentelle Untersuchungen zur Wundheilung in den Nasennebenholhlen. II. Spontaner Wundschluss and medikamentose Effekte im standardisierten Wundmodell.' HNO 39 (1991) pp. 48-54.

(56) References Cited

OTHER PUBLICATIONS

Hosemann W.G. et al Minimally Invasive Endonasal Sinus Surgery Thieme, Stuttgart, New York (2000) [Summary of textbook].
Hosemann, M.E. et al 'Normal Wound Healing of the Paranasal Sinuses—Clinical and Experimental Investigations' Eur Arch Otorhinolarygol. (1991) vol. 248 pp. 390-394.
Hosemann, W. et al 'Weiterbehandlung nach Nasennebenhohleneingriffen, Part 2: Therapeutische Maßnahmen' HNO akutell 7 (1999) pp. 291-302.
Ijaduola, T.G.A. 'Use of a Foley Catheter for Short-Term Drainage in Frontal Sinus Surgery' The Journal of Laryngology and Otology. (1989) vol. 103 pp. 375-378.
Ingals, E.F. 'New Operation and Instruments for Draining the Frontal Sinus' Ann. Otol Rhinol Laryngol. (1905) vol. 14 pp. 515-519.
Iro, H. et al 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. (1997) vol. 107 pp. 1-36.
Khomutov, S.M. et al 'Dissolution of a Mixture of Steroids in Cyclodextrin Solutions: a Model Description' Pharmaceutical Chemistry Journal. (Nov. 2001) vol. 35, No. 11 pp. 627-629.
Kingdom, T.T. et al 'Image-Guided Surgery of the Sinuses: Current Technology and Applications' Otolaryngol. Clin. North Am. (Apr. 2004) vol. 37, No. 2 pp. 381-400.
Klossek, J.M. et al 'Local Safety of Intranasal Triamcinolone Acetonide: Clinical and Histological Aspects of Nasal Mucosa in the Long-Term Treatment of Perennial Allergic Rhinitis' Rhinology (2001) vol. 39, No. 1 pp. 17-22.
Kozlov et al 'Diagnosis and Treatment of Sinusitis by YAMIK Sinus Catheters' Rhinology (1996) vol. 34. pp. 123-124.
Laliberte F. et al 'Clinical and Pathologic Methods to Assess the Long-Term Safety or Nasal Corticosteroids' Allergy (2000) vol. 55, No. 8 pp. 718-722.
Lang, E.V. et al 'Access Systems for Puncture at an Acute Angle' J. Vasc. Interv. Radiol. (1995) vol. 6, No. 5 pp. 711-713.
Large, G.C. 'Crystalline Tetracycline Hydrochloride in the Treatment of Acute and Chronic Maxillary Sinusitis' Canad. M. A. J. (1958) vol. 79 pp. 15-16.
Lund, V.J. 'Maximal Medical Therapy for Chronic Rhinosinusitis' Otolaryngol Clin N Am. (2005) vol. 38 pp. 1301-1310.
Maran, A.G.D. et al 'The Use of the Foley Catheter in the Tripod Fracture' J. Laryngol. Otor (1971) vol. 85, Issue 9 pp. 897-902.
May, M. et al 'Frontal Sinus Surgery: Endonasal Drainage Instead of an External Osteopolstic Approach' Op Tech Otolaryngo Head Neck Surgery (1995) vol. 6, No. 3 pp. 184-192.
Medtronic, xomed.com—MircoFrance Catalog Browser. http://www.xomcat.com/xomfrance/index.php?zone=both&cat=18&sub=58&prodline=1272 (Dec. 31, 2003) pp. 1-2.
Mehan, V.K. et al 'Coronary Angioplasty through 4 French Diagnostic Catheters' Cathet. Cardiovasc. Diagn. (1993) vol. 30, No. 1 pp. 22-26.
Metson, R. et al 'Endoscopic Treatment of Sphenoid Sinusitis' Otolaryngol. Head Neck Surg. (1996) vol. 114, No. 6 pp. 736-744.
Metson, R. 'Holmium: YAG Laser Endoscopic Sinus Surgery: A Randomized Controlled Study' Laryngoscope (Jan. 1996) vol. 106, Issue 1, Supplement 77 pp. 1-18.
Mols, B. 'Moveable Tool Tip for Keyhole Surgery' Delft Outlook (2005) vol. 3 pp. 13-17.
Mooney, M.R. et al 'Monorail™Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al 'Addition-Elimination Reaction in the Trifluoroacetylation of Electron-Rich Olefins' J. Org. Chem. (1995) vol. 60, No. 11 pp. 3523-3528. American Chemical Society.
Park, K. et al Biodegreadable Hydrogels for Drug Delivery (1993) Technomic Publishing Inc. Lancaster [Summary of textbook].
Piccirillo, J.F. et al 'Psychometric and Clinimetric Validity of the 20-Item Sino-Nasal Outcome Test (SNOT-20)' Otolaryngol. Head Neck Surg (2002) vol. 126, No. 1 pp. 41-47.
Piers, et al 'A Flexible Distal Tip with Two Degrees of Freedom for Enhanced Dexterity in Endoscopic Robot Surgery' Proceedings 13th Micromechanics Europe Workshop (2002) pp. 271-274.
Podoshin, L. et al 'Balloon Technique for Treatment of Frontal Sinus Fractures' The Journal of Laryngology & Otology (1967), vol. 81. pp. 1157-1161.
Pownell, P.H. et al 'Diagnostic Nasal Endoscopy' Plastic & Reconstructive Surgery (1997) vol. 99, Iss. 5 pp. 1451-1458.
Prince et al 'Analysis of the Intranasal Distribution of Ointment' J Otolaryngol. (1997) vol. 26 pp. 357-360.
Ramsdale, D.R. *Illustrated Coronary Intervention a case-oriented approach* (2001) Martin Dunitz Ltd. pp. 1-5.
Ritter, F.N. et al *Atlas of Paranasal Sinus Surgery* (1991) Igaku-Shoin Medical Pub. pp. 1-81.
Sama, A. et al 'Current Opinions on the Surgical Management of Frontal Sinus Disease' ENT News. www.pinpointmendical.com/ent-news (2009) vol. 17, No. 6 pp. 60-63.
Sanborn, T.A., et al 'Percutaneous Endocardial Transfer and Expression of Genes to the Myocardium Utilizing Fluroposcopic Guidance' Catheter Cardiovasc. Interv. (2001) vol. 52, No. 2 pp. 260-266.
*Sawbones Catalog* 2001, Pacific Research Laboratories, Inc., Vashon, Washington 98070 USA.
Saxon, R.R., et al 'Technical Aspects of Accessing the Portal Vein During the Tips Procedure' J. Vasc. Interv. Radiol. (1997) vol. 8, No. 5 pp. 733-744.
Schneider. Pfizer Ad for Softip. [date of publication unknown].
Shah, N. J. et al 'Endoscopic Pituitary Surgery—A Beginner's Guide' Indian Journal of Otolaryngology and Head and Neck Surgery (2004) vol. 56, No. 1 pp. 71-78.
Shah, N. J. 'Functional Endoscopic Sinus Surgery' (1999); found at www.bhj.org/journal/1999_4104_oct99/sp_659.htm.
St. Croix, et al 'Genes Expressed in Human Tumor Endothelium' Science (May 15, 2000) vol. 289 pp. 1197-1202.
Stammberger H. 'Komplikationen entzundlicher Nasennebenhohlenerkrankungen eischließlich iatrogen bedingter Komplikationen.' Eur Arch Oti-Rhino-Laryngol Suppl. (Jan. 1993) pp. 61-102.
Strohm, et al 'Le Traitement Des Stenoses Voies Aeriennes Superieures Par Dilation Au Balloon' Sep. 25, 1999.
SurgTrainer Product Information 'Incisive Human Nasal Model for ESS Training' Surg. Trainer, Ltd. Ibaraki, Japan (2004) http://www1.accsnet.ne.jp/~juliy/st/en/partslist.html.
Tabor, M.H. et al 'Symptomatic Bilateral Nasolacrimal Duct Cysts in a Newborn-Rhinoscopic Clinic' Ear, Nost & Throat Journal (2003) http://findarticles.com/p/articles/mi_mOBUM/is_2_82/ai_98248244 pp. 1-3.
Terumo. Medi-Tech. Boston Scientific. (1993) Ad for Glidewire.
The Operating Theatre Journal (www.otjonline.com) 'Disposable Medical Device for Wound Disclosure/The Tristel Purple Promotion—A Collaboration between Tristel plc and Karl Storz Endoscopy (UK) Ltd.' pp. 4. [retrieved on Nov. 30, 2010]. Retrieved from the Internet.
Weber, R. et al 'Endonasale Stirnhohlenchirugie mit Langzeiteinlage eines Platzhalters' Laryngol. Rhinol. Otol. (1997) vol. 76 pp. 728-734. (English Abstract).
Weber, R. et al 'Videoendscopic Analysis of Nasal Steroid Distribution' Rhinology (1999) vol. 37 pp. 69-73.
Weiner, R.I., D.O. et al 'Development and Application of Transseptal Left Heart Catheterization' Cathet. Cardiovasc. Diagn. (1988) vol. 15, No. 2 pp. 112-120.
Wiatrak, B.J. et al 'Unilateral Choanal Atresia: Initial Presentation and Endoscopic Repair' International Journal of Pediatric Otorhinolaryngology (1998) vol. 46 pp. 27-35.
Wormald, P.J. et al 'The 'Swing-Door' Technique for Uncinectomy in Endoscopic Sinus Surgery' The Journal of Laryngology and Otology (1998) vol. 112 pp. 547-551.
Xomed-Treace. Bristol-Myers Squibb. Ad for Laser Shield II. Setting the Standards for Tomorrow. [date of publication unknown].
Yamauchi, Y. et al 'Development of a Silicone Model for Endoscopic Sinus Surgery' proc International Journal of Computer Assisted Radiology and Surgery (1999) vol. 99 pp. 1039.

(56) References Cited

OTHER PUBLICATIONS

Yamauchi, Y. et al 'A Training System for Endoscopic Sinus Surgery with Skill Evaluation' Computer Assisted Radiology and Surgery (2001) with accompanying copy of poster presentation.
Yanagisawa et al 'Anterior and Posterior Fontanelles.' Ear, Nose & Throat Journal (2001) vol. 80. p. 10-12.
Zimarino, M., MD et at 'Initial Experience with the EuropassTM: A New Ultra-Low Profile Monorail Balloon Catheter' Cathet. Cardiovasc. Diagn. (1994) vol. 33, No. 1 pp. 76-79.
http://www.invotec.net/rhinology/ksplint.html. K-Splint Internal Nasal Splints; Jan. 25, 2007.
http://www.doylemedical.com/nasalsplints.htm; Doyle Nasal Splints; Jan. 25, 2007.
http://www.technologyforlife.com.au/ent/nasal.html; Nasal Surgery and Accessories; Jan. 25, 2007.
EP Communication dated Sep. 4, 2008 re: EP 05773189.
EP Communication dated Jun. 19, 2009 re: EP 05773189.
Examination Report dated Feb. 22, 2006 re: 02716734.5.
Examination Report dated Feb. 8, 2007 re: 02716734.5.
Examiners First Report dated Apr. 8, 2010 re: AU2005274794.
European Search Report and Search Opinion dated Sep. 11, 2009 from EP06815174.
European Search Report dated Sep. 27, 2011 re: EP10182961.
International Preliminary Report on Patentability dated Aug. 25, 2006 from PCT/US05/25371.
International Preliminary Report on Patentability dated Oct. 4, 2007 from PCT/US06/002004.
International Preliminary Report on Patentability dated Nov. 27, 2008 from PCT/US07/11449.
International Preliminary Report on Patentability dated Apr. 16, 2009 from PCT/US07/021170.
International Preliminary Report on Patentability dated May 14, 2009 from PCT/US06/36960.
International Preliminary Report on Patentability dated Oct. 22, 2009 from PCT/US08/059786.
International Preliminary Report on Patentability dated Nov. 5, 2009 from PCT/US08/061343.
International Search Report dated May 23, 2002 from PCT/EP02/01228.
International Search Report and Written Opinion dated Apr. 10, 2006 from PCT/US05/25371.
International Search Report dated May 8, 2007 from PCT/US2006/16026.
International Search Report and Written Opinion dated Aug. 17, 2007 from PCT/US05/13617.
International Search Report dated Sep. 25, 2007 from PCT/US06/37167.
International Search Report dated Oct. 19, 2007 from PCT/US07/03394.
International Search Report and Written Opinion dated May 29, 2008 from PCT/US07/021170.
International Search Report dated May 29, 2008 from PCT/US07/21922.
International Search Report and Written Opinion dated Jul. 1, 2008 from PCT/US06/22745.
International Search Report dated Jul. 3, 2008 from PCT/US2006/029695.
International Search Report dated Jul. 7, 2008 from PCT/US07/16213.
International Search Report dated Jul. 8, 2008 from PCT/US07/11474.
International Search Report and Written Opinion dated Jul. 17, 2008 from PCT/US06/36960.
International Search Report and Written Opinion dated Jul. 21, 2008 from PCT/US05/33090.
International Search Report dated Aug. 25, 2008 from PCT/US2008/000911.
International Search Report dated Sep. 10, 2008 dated PCT/US07/16212.
International Search Report and Written Opinion dated Sep. 12, 2008 from PCT/US07/16214.
International Search Report and Written Opinion dated Sep. 17, 2008 from PCT/U S08/059786.
International Search Report and Written Opinion dated Sep. 17, 2008 from PCT/US08/061343.
International Search Report and Written Opinion dated Oct. 1, 2008 from PCT/US07/11449.
International Search Report dated Oct. 15, 2008 from PCT/US2008/061048.
International Search Report from PCT Application No. PCT/US2009/057203 dated Nov 30, 2009 as issued by the European Patent Office as searching authority.
International Search Report dated Dec. 10, 2009 re: PCT/US2009/052236.
International Search Report dated Dec. 16, 2009 re: PCT/US2009/050800.
International Search Report dated Mar. 31, 2010 re: PCT/US2009/069143.
International Search Report dated Jul. 8, 2010 re: PCT/US2010/027837.
International Search Report dated Oct. 6, 2010 re: PCT/US2010/040548.
International Search Report dated Mar. 25, 2011 re: PCT/US2010/062161.
International Search Report dated Mar. 28, 2011 re: PCT/US2010/061850.
International Search Report dated Mar. 31, 2011 re: PCT/US2010/060898.
International Search Report dated Aug. 9, 2011 re: PCT/US2011/038751.
Partial European Search Report dated Sep. 20, 2007 re: 07252018.
Partial European Search Report dated Mar. 25, 2008 re: 07252018.
Supplemental European Search Report dated Jun. 2, 2008 re: EP05773189.
Supplemental European Search Report dated Jul. 1, 2009 re: EP06815285.
Supplemental European Search Report dated Jan. 29, 2010 from EP07836108.
Supplemental European Search Report dated Feb. 2, 2010 re: EP07836109.
Supplemental European Search Report dated Feb. 17, 2010 re: EP07836110.
Supplemental European Search Report dated Mar. 1, 2010 re: EP05778834.
Supplemental European Search Report dated Mar. 16, 2010 from EP06718986.
Supplemental European Search Report dated Jun. 22, 2010 re: EP06784759.
Supplemental European Search Report dated Sep. 23, 2010 re: EP08746715.
Supplemental Partial European Search Report dated Nov. 19, 2010 re: EP06751637.
Supplemental European Search Report dated Jan. 28, 2011 re: 07777004.
Supplemental European Search Report dated Mar. 31, 2011 re: EP05798331.
Supplemental European Search Report dated Aug. 30, 2011 re: EP06800540.
Supplemental European Search Report dated Sep. 29, 2011 re: EP07750248.
U.S. Appl. No. 10/259,300, filed Sep. 30, 2002.
U.S. Appl. No. 10/259,630, filed Sep. 30, 2002.
U.S. Appl. No. 10/470,881, filed Feb. 4, 2004.
U.S. Appl. No. 11/116,118, filed Apr. 26, 2005.
U.S. Appl. No. 11/193,020, filed Jul. 29, 2005.
U.S. Appl. No. 11/234,395, filed Sep. 23, 2005.
U.S. Appl. No. 11/347,147, filed Feb. 2, 2006.
U.S. Appl. No. 11/355,512, filed Feb. 16, 2006.
U.S. Appl. No. 11/436,892, filed May 17, 2006.
U.S. Appl. No. 11/436,897, filed May 17, 2006.
U.S. Appl. No. 11/438,090, filed May 18, 2006.
U.S. Appl. No. 11/522,497, filed Sep. 15, 2006.

(56) References Cited

OTHER PUBLICATIONS

U.S. Appl. No. 11/647,530, filed Dec. 27, 2006.
U.S. Appl. No. 11/655,794, filed Jan. 18, 2007.
U.S. Appl. No. 11/725,151, filed Mar. 15, 2007.
U.S. Appl. No. 11/789,705, filed Apr. 24, 2007.
U.S. Appl. No. 11/803,695, filed May 14, 2007.
U.S. Appl. No. 11/926,565, filed Oct. 29, 2007.
U.S. Appl. No. 12/011,100, filed Jan. 23, 2008.
U.S. Appl. No. 12/100,361, filed Apr. 9, 2008.
U.S. Appl. No. 12/117,582, filed May 8, 2008.
U.S. Appl. No. 12/117,672, filed May 8, 2008.
U.S. Appl. No. 12/117,961, filed May 9, 2008.
U.S. Appl. No. 12/118,931, filed May 12, 2008.
U.S. Appl. No. 12/120,902, filed May 15, 2008.
U.S. Appl. No. 12/122,884, filed May 19, 2008.
U.S. Appl. No. 12/340,226, filed Dec. 19, 2008.
U.S. Appl. No. 12/341,602, filed Dec. 22, 2008.
U.S. Appl. No. 12/502,101, filed Jul. 13, 2009 15, 2006.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
USPTO Office Action dated Nov. 17, 2008 in U.S. Appl. No. 12/117,582.
USPTO Office Action dated Nov. 17, 2008 in U.S. Appl. No. 12/118,931.
USPTO Office Action dated Feb. 4, 2009 in U.S. Appl. No. 11/347,147.
USPTO Office Action dated Mar. 23, 2009 in U.S. Appl. No. 11/804,309.
USPTO Office Action dated Mar. 23, 2009 in U.S. Appl. No. 11/926,326.
USPTO Office Action dated Jul. 30, 2009 in U.S. Appl. No. 12/118,931.
USPTO Office Action dated Aug. 6, 2009 in U.S. Appl. No. 11/347,147.
USPTO Office Action dated Aug. 6, 2009 in U.S. Appl. No. 12/117,582.
USPTO Office Action dated Aug. 6, 2009 in U.S. Appl. No. 12/117,961.
USPTO Office Action dated Oct. 21, 2009 in U.S. Appl. No. 12/120,902.
Deutschmann, R. et al. 'A Contribution to the Topical Treatment of [Maxillary] Sinusitis Preliminary Communication' Stomat DDR 26, (1976) pp. 585-592.
Gottman, et al. 'Balloon Dilatation in the Nasal Cavity and Paranasal Sinuses' CIRSE. (Sep. 25, 2004) pp. 1-27.
Gottman, et al. 'Successful Treatment of Recurrent Post-Operative Frontal Sinus Stenoses by Balloon Dilatation' CIRSE. (Oct. 5, 2002).
Hosemann, W. et al 'Weiterbehandlung nach Nasen-nebenhohleneingriffen, Part 2: Theapeutische Maβnahmen' HNO akutell 7 (1999) pp. 291-302.
Fletcher, I.E., "New Operation and Instruments for Draining the Frontal Sinus" Ann. Otol Rhino Laryngol. (1905) vol. 14, pp. 151-519.
Good, R.H. "An Intranasal Method for Opening the Frontal Sinus Establishing the Largest Possible Drainage" Laryngoscope (1908) vol. 18 pp. 266-274.
Hojo, M. et al, "Electrophilic Substitutions of Olefinic Hydrogens II. Acylation of Vinyl Ethers and N Vinyl Amides" Chemistry Letters (1976) pp. 499-502.
Hosemann, W. et al. "Endonasal Frontal Sinusotomy in Surgical Management of Chronic Sinusitis: A Critical Evaluation" American Journal of Rhinology (1997) vol. 11, No. 1 pp. 1-9.
US Office Action dated Aug. 6, 2009 re. U.S. Appl. No, 12/117,961.
International Preliminary Report on Patentability dated Feb. 15, 2008 from PCT/US05/13617.
International Search Report and Written Opinion dated Aug. 29, 2007 from PCT/US06/002004.

Barrett, Steven; Be Wary of Neurocranial Restructuring (NCR). Chirobase (available at: http://www.chirobase.org/06DD/ncr.html) Jul. 2003.
Benninger, et al.; Adult Chronic Rhinosinusitis: definitions, diagnosis, epidemiology, and pathophysiology; Arch Otolarygol Head and Neck Sug; vol. 129, p. S1-S22; Sep. 2003.
Benninger, et al.; Adult Chronic Rhinosinusitis: definitions, diagnosis, epidemiology, and pathophysiology; Arch Otolarygol Head and Neck Sug; vol. 129, p. S1-S32; Sep. 2003.
Bent et al., The Frontal Cell as a Cause of Frontal Sinus Obstruction, American Journal of Rhinology, vol. 8, No. 4, 1994, pp. 185-191.
Binner, et al., Fibre-Optic Transillumination of the Sinuses: A Comparison of the Value of Radiography and Transillumination in Antral Disease, Clinical Otolaryngology, 1978, 3, pp. 1-11.
Casiano, et al., Endoscopic Lothrop Procedure: The University of Miami Experience, American Journal of Rhinology, vol. 12, No. 5, 1998, pp. 335-339.
Colla, A., et al 'Trihaloacetylated Enol Ethers-General Synthetic Procedure and Heterocyclic Ring Closure Reactions with Hydroxylamine' Synthesis Jun. 1991 pp. 483-486.
Croix, et al.; "Genes Expressed in Human Tumor Endothelium"; Science vol. 289 pp. 1197-1202; May 15, 2000.
Davis, Greg E., et al., A Complication From Neurocranial Restructuring; Arch Otolaryngol Head Neck Surg; vol. 129, p. 472-474; Apr. 2003.
Deutschmann, R. et al., A Contribution to the Topical Treatment of [Maxillary] Sinusitis Preliminary Communication, Stomat DDR 26 (1976), 585-592.
Friedman, et al., Intraoperative and Postoperative Assessment of Frontal Sinus Patency by Transillumination, Laryngoscope 110: Apr. 2000, pp. 683-684.
Friedman, M. M.D., et al, 'Operative Techniques in Otolaryngology-Head and Neck Surgery' vol. 12, No. 2, Jun. 2001, pp. 60-65.
Gerus, I.I. et al β-Ethoxyvinyl Polyfluroroalkyl Ketones-Versatile Synthones in Fluoroorganic Chemistry Journal of Fluorine Chemistry (1994) pp. 195-198, vol. 69 Elsevier Science S.A.
Gorlov, D.V. et al 'Acylation of 2-Methoxypropene with Anhydrides and Halides of Perflurocarboxylic Acids in the Presence of Tertiary Amities' Russian Chemical Bulletin, Sep. 1999, pp. 1791-1792 vol. 48 No. 9, Kluwer Academic/Plenum Publishers.
Gottrnan, et al., Balloon dilatation in the nasal cavity and paranasal sinuses; CIRSE, Sep. 25, 2004.
Gottman, et al., Balloon dilatation in the nasal cavity and paranasal sinuses; CIRSE, Sep. 25, 2004. pp. 1-27.
Gottman, et al., Balloon Dilatation of Recurrent Ostial Occlusion of the Front Sinus ECR, Mar. 2, 2001.
Gottman, et al., Balloon Dilatation of Recurrent Ostial Occlusion of the Front Sinus; Abstract No. B-04353. European Congress of Radiology, Mar. 2, 2001.
Gottman, et al., Balloon Dilatation of Recurrent Ostial Occlusion of the Front Sinus; Abstract No. B-04353. European Congress of Radiology, Mar. 2, 2001, pp. 1-4.
Gottman, et al., Balloon Dilatation of Recurrent Ostial Occlusion of the Front Sinus. European Congress of Radiology, Mar. 2, 2001. pp. 1-57.
Gottman, et al., Successful Treatment of Recurrent Post-Operative Frontal Sinus Stenoses by Balloon Dilatation; CIRSE, Oct. 5, 2002.
Hospital Corpsman Sickcall Screener's Handbook Naval Hospital Great Lakes. http://www.brooksidepress.org/Products/Operationa.Medicine/DATA.2001 pp. 1-6.
Hybels, Transillumination During Osteoplastic Frontal Sinusotomy, The Laryngoscope 91: Sep. 1981, p. 1560.
Kennedy, D.W., MD et al 'Diseases of the Sinuses Diagnosis and Management' Copyright 2001 by B.C. Decker Inc.
Kuhn, et al., The Agger Nasi Cell in Frontal Recess Obstruction: An Anatomic, Radiology and Clinical Correlation, Operative Techniques in Otolaryngology-Head and Neck Surgery, vol. 2, No. 4, 1991, pp. 226-231.
Lanza, Donald C., Postoperative Care and Avoiding Frontal Recess Stenosis, International Advanced Sinus Symposium, Jul. 21-24, 1993.

(56) References Cited

OTHER PUBLICATIONS

Masaru H. et al 'Electrophilic Substitutions of Olefinic Hydrogens II. Acylation of Vinyl Ethers and N Vinyl Amides Chemistry Letters' 1976 pp. 499-502, Chemical Society of Japan.
Medtronic, xomed.com-MicroFrance Catalog Browser. http://222.xomcat.com/xomfrance/index.php?zone=dom&cat-18&s. Dec. 31, 2003 pp. 1-2.
Mellor, J.M. et al 'Synthesis of Trifluromethylnaphthalenes' Tetraheron, 56 (2000), pp. 10067-10074, Elseview Science Ltd.
Miller, et al., Management of Fractures of the Supraorbital Rim, the Journal of Trauma, vol. 18, No. 7, pp. 507-512, Jul. 1978.
Min, Yang-Gi et al., Mucociliary Activity and Histopathology of Sinus Mucosa in Experimental Maxilary Sinusitis: A Comparison of Systemic Administration of Antibiotic and Antibiotic Delivery by Polylactic Acid Polymer, Laryngoscope, Aug. 1995, 105:835-842.
Robison, J. Mathews, M.D., Pressure Treatment of Maxillary Sinusitis, J.A.M.A., May 31, 1952, pp. 436-440.
Robison, J. Mathews, M.D., Pressure Treatment of Purulent Maxillary Sinusitis, Texas State Journal of Medicine, May 1951, pp. 281-288.
Schaefer, S.D., M.D. 'Rhinology and Sinus Disease A Problem-Oriented Approach' Copyright 1988 by Mosby, Inc.
Single-Pole and Multi-Pole Lightguides for UV Spot Light Curing Systems. http://www.dymax.cona/products/curing_equipment/lightguids/light. 2004 pp. 1-2.
Sinusitis, Maxillary, Acute Surgical Treatment. http://www.emedicine.com/ent/topic340.htm. Aug. 29, 2006. pp. 1-11.
Stammberger, et al., Special Endoscopic Anatomy of the Lateral Nasal Wall and Ethmoidal Sinuses, Functional Endoscopic Sinus Surgery, 1991, Ch. 3, pp. 49-87.K.
Strohm et al. Die Behandlung von Stenosen der oberen Luftwege mittels rontgenologisch gesteuerter Ballondilation Sep. 25, 1999.
Strohm et al. Die Behandlung von Stenosen der oberen Luftwege mittels rontgenologisch gesteuerter Ballondilation, pp. 1-4, Sep. 25, 1999.
Strohm, et al 'Treatment of the Stenoses of the Upper Air Routes by Balloon Dilation' Sudwestdeutscher Abstract 45, Sep. 25, 1999 pp. 1-3.
Takeshi, M. et al 'Addition-Elimination Reaction in the Trifluoroacetylation of Electron-Rich Olefins' J. Org. Chem. (1995), pp. 3523-3528, vol. 60, No. 11. American Chemical Society.
Tarasov, D.I. et al., Application of Drugs Based on Polymers in the Treatment of Acute and Chronic Maxillary Sinusitis, Vestn Otorinolaringol. (1978), vol. 6, pp. 45-47.
Woog, et al., Paranasal Sinus Endoscopy and Orbital Fracture Repair, Arch Ophthalmol, vol. 116, May 1998, pp. 688-691.
PCT Search Report from PCT Application No. PCT/US2009/057203 dated Nov. 30, 2009 as issued by the European Patent Office as searching authority.
U.S. Appl. No. 10/829,917, filed Jul. 16, 2004.
U.S. Appl. No. 10/912,578, filed Aug. 4, 2004.
U.S. Appl. No. 10/944,270, filed Sep. 17, 2004.
U.S. Appl. No. 11/037,548, filed Jan. 18, 2005.
U.S. Appl. No. 11/150,847, filed Jun. 10, 2005.
U.S. Appl. No. 11/527,773, filed Sep. 25, 2006.
U.S. Appl. No. 11/544,009, filed Oct. 4, 2006.
U.S. Appl. No. 11/648,159, filed Dec. 29, 2006.
U.S. Appl. No. 11/789,704, filed Apr. 24, 2007.
U.S. Appl. No. 11/925,540, filed Oct. 26, 2007.
U.S. Appl. No. 11/926,326, filed Oct. 29, 2007.
U.S. Appl. No. 11/928,097, filed Oct. 30, 2007.
USPTO Office Action dated Sep. 16, 2005 in U.S. Appl. No. 10/259,300.
USPTO Office Action dated Jul. 7, 2006 in U.S. Appl. No. 10/259,300.
USPTO Office Action dated Feb. 13, 2007 in U.S. Appl. No. 10/259,300.
USPTO Office Action dated May 29, 2007 in U.S. Appl. No. 10/912,578.
USPTO Office Action dated Oct. 9, 2007 in U.S. Appl. No. 10/259,300.
USPTO Office Action dated Oct. 18, 2007 in U.S. Appl. No. 11/037,548.
USPTO Office Action dated Nov. 14, 2007 in U.S. Appl. No. 10/912,578.
USPTO Office Action dated Nov. 28, 2007 in U.S. Appl. No. 11/234,395.
USPTO Office Action dated Dec. 6, 2007 in U.S. Appl. No. 11/037,548.
USPTO Office Action dated Dec. 10, 2007 in U.S. Appl. No. 10/912,578.
USPTO Office Action dated Jan. 24, 2008 in U.S. Appl. No. 10/259,300.
USPTO Office Action dated Apr. 9, 2008 in U.S. Appl. No. 11/037,548.
USPTO Office Action dated Sep. 12, 2008 in U.S. Appl. No. 10/829,917.
USPTO Office Action dated Oct. 6, 2008 in U.S. Appl. No. 10/259,300.
USPTO Office Action dated Oct. 29, 2008 in U.S. Appl. No. 11/347,147.
USPTO Office Action dated Nov. 7, 2008 in U.S. Appl. No. 10/944,270.
USPTO Office Action dated Nov. 17, 2008 in U.S. Appl. No. 10/829,917.
USPTO Office Action dated Nov. 25, 2008 in U.S. Appl. No. 12/117,961.
USPTO Office Action dated Dec. 5, 2008 in U.S. Appl. No. 12/120,902.
USPTO Office Action dated Jan. 28, 2009 in U.S. Appl. No. 10/944,270.
USPTO Office Action dated Mar. 3, 2009 in U.S. Appl. No. 12/117,582.
USPTO Office Action dated Mar. 4, 2009 in U.S. Appl. No. 12/118,931.
USPTO Office Action dated Mar. 17, 2009 in U.S. Appl. No. 11/690,127.
USPTO Office Action dated Mar. 18, 2009 in U.S. Appl. No. 10/829,917.
USPTO Office Action dated Apr. 21, 2009 in U.S. Appl. No. 10/944,270.
USPTO Office Action dated Aug. 28, 2009 in U.S. Appl. No. 11/150,847.
USPTO Office Action dated Nov. 9, 2009 in U.S. Appl. No. 10/829,917.
Chien, Y.W. et al., Nasal Systemic Drug Delivery (Drugs and the Pharmaceutical Sciences), vol. 39, Jun. 28, 1989, pp. 60-63.
Gottmann, D. et al., "Balloon Dilatation of Recurrent Ostial Occlusion of the Frontal Sinus, Abstract", OASIS Online Abstract Submission and Invitation System, Coe-Truman Technologies, Inc., Mar. 2001.
Australian Patent Examination Report dated Aug. 24, 2012 for Application No. AU 2012201954.
Canadian Examination Report dated Jul. 19, 2013 for Application No. CA 2,575,361.
European Search Report and Written Opinion dated Oct. 6, 2011 for Application No. EP 10182961.2.
International Search Report dated Aug. 29, 2007 for Applicaton No. PCT/US2006/002004.
Japanese Notice of Rejection dated Feb. 15, 2011 for Application No. JP 2007-524827.
Japanese Notice of Rejection dated Dec. 27, 2012 for Application No. JP 2007-524827.
Japanese Notice of Rejection dated Jul. 30, 213 for Application No. JP 2012-165578.

\* cited by examiner

IMPLANTABLE DEVICES AND METHODS FOR DELIVERING DRUGS AND OTHER SUBSTANCES TO TREAT SINUSITIS AND OTHER DISORDERS

RELATED APPLICATION

This application is a division of Ser. No. 10/912,578 filed Aug. 4, 2004 now U.S. Pat. No. 7,361,168, the entire disclosure of which is expressly incorporated herein by reference.

FIELD OF THE INVENTION

The present invention relates generally to medical devices and methods and more particularly to substance delivering implants and methods for treating a broad range of disorders including but not limited to sinusitis and other ear, nose and throat disorders.

BACKGROUND

The paranasal sinuses are cavities formed within the bones of the face. The paranasal sinuses include frontal sinuses, ethmoid sinuses, sphenoidal sinuses and maxillary sinuses. The paranasal sinuses are lined with mucous-producing epithelial tissue. Normally, mucous produced by the linings of the paranasal sinuses slowly drains out of each sinus through an opening known as an ostium, and into the nasopharnyx. Disorders that interfere with drainage of mucous (e.g., occlusion of the sinus ostia) can result in a reduced ability of the paranasal sinuses to function normally. This results in mucosal congestion within the paranasal sinuses. Such mucosal congestion of the sinuses can cause damage to the epithelium that lines the sinus with subsequent decreased oxygen tension and microbial growth (e.g., a sinus infection).

The nasal turbinates are three (or sometimes four) bony processes that extend inwardly from the lateral walls of the nose and are covered with mucosal tissue. These turbinates serve to increase the interior surface area of the nose and to impart warmth and moisture to air that is inhaled through the nose. The mucosal tissue that covers the turbinates is capable of becoming engorged with blood and swelling or becoming substantially devoid of blood and shrinking, in response to changes in physiologic or environmental conditions. The curved edge of each turbinate defines a passageway known as a meatus. For example, the inferior meatus is a passageway that passes beneath the inferior turbinate. Ducts, known as the nasolacrimal ducts, drain tears from the eyes into the nose through openings located within the inferior meatus. The middle meatus is a passageway that extends inferior to the middle turbinate. The middle meatus contains the semilunar hiatus, with openings or ostia leading into the maxillary, frontal, and anterior ethmoid sinuses. The superior meatus is located between the superior and medial turbinates.

Nasal polyps are benign masses that grow from the lining of the nose or paranasal sinuses. Nasal polyps often result from chronic allergic rhinitis or other chronic inflammation of the nasal mucosa. Nasal polyps are also common in children who suffer from cystic fibrosis. In cases where nasal polyps develop to a point where they obstruct normal drainage from the paranasal sinuses, they can cause sinusitis.

The term "sinusitis" refers generally to any inflammation or infection of the paranasal sinuses. Sinusitis can be caused by bacteria, viruses, fungi (molds), allergies or combinations thereof.

Various drugs have been used to treat sinusitis, including systemic antibiotics. Intranasal corticosteroid sprays and intranasal decongestant sprays and drops have also been used. However, the use of intranasal sprays and drops by most patients does not result in the drug actually entering the affected intranasal sinuses. Rather, such sprays and drops typically contact only tissues located within the nasal cavity. The introduction of drugs directly into the sinuses has been proposed by others, but has not become a widely used treatment technique.

For example, United States Patent Application Publication 2004/0116958A1 (now U.S. Pat. No. 8,740,929) (Gopferich et al.) describes a tubular sheath or "spacer" formed of biodegradable or non-biodegradable polymer that, prior to insertion in the patient's body, is loaded with a controlled amount of an active substance, such as a corticosteroid or anti-proliferative agent. Surgery is performed to create a fenestration in a frontal sinus and the sheath is inserted into such fenestration. Thereafter, the sheath which has been preloaded with the active substance is inserted into the surgically created fenestration where it a) deters closure of the surgically created fenestration, b) serves as a conduit to facilitate drainage from the sinus and d) delivers the active substance. The sheath of United States Patent Application Publication 2004/0116958A1 (now U.S. Pat. No. 8,740,929) (Gopferich et al.) remains substantially in a single configuration (i.e., it does not transition between a collapsed configuration and an expanded configuration) although it may be coated with a material that swells when in contact with mucous or body fluid. In some embodiments, the sheath is formed of multiple layers of polymeric material, one or more of which is/are loaded with the active substance and one or more of which is/are free of the active substance. In other embodiments, the sheath has a "hollow body" which forms a reservoir system wherein the active substance is contained and a membrane which controls the release of the active substance from the reservoir. In some embodiments, the sheath may be anchored by causing the end of the sheath that extends into the sinus to swell or otherwise enlarge.

Also, Min, Yang-Gi, et al., *Mucociliary Activity and Histopathology of Sinus Mucosa in Experimental Maxilary Sinusitis: A Comparison of Systemic Administration of Antibiotic and Antibiotic Delivery by Polylactic Acid Polymer*, Laryngoscope, 105:835-842 (August 1995) describes experiments wherein experimental sinusitis was induced in three groups of rabbits by "pasting" the natural sinus ostia, forming an incision and small bore hole made in the anterior wall of the sinus, introducing pathogenic microbes through the bore hole and then closing the incision. Five days after introduction of the pathogenic microbes, the natural sinus ostia were reopened and the rabbits were divided into three (3) groups. Group 1 (control) received no treatment. Group 2 received repeated intramuscular injections of ampicillin. In the animals of Group 3, 1.5 cm×1.5 cm sheets of polylactic acid polymer (PLA) film containing ampicillin (0.326 mg/sheet) were roiled up and inserted through the natural ostia into the infected sinuses. Thereafter, measurements of mucocilliary transport speed were made and the tissues lining the affected sinuses were examined histopathologically. The authors concluded that the therapeutic effect observed in the animals that had received intrasinus implants of PLA/Ampicillin film (Group 3) was significantly better that that observed in the untreated control animals (Group 1) or those that has received repeated intramuscular doses of ampicillin (Group 2).

U.S. Pat. No. 3,948,254 (Zaffaroni) describes implantable drug delivery devices comprising a drug reservoir surrounded by a microporous wall. The reservoir may be formed of a solid drug carrier that is permeable to passage of the drug. The rate of passage of the drug through the wall may be slower than the rate at which the drug passes through the solid drug carrier that forms the reservoir. U.S. Pat. No. 3,948,254 (Zaffaroni) describes a number of applications for the implantable drug delivery devices including placement in a nasal passage. Specifically, U.S. Pat. No. 3,948,254 (Zaffaroni) claimed a nasal delivery device for dispensing a drug within a nasal passage at a controlled rate wherein the nasal device is comprised of (a) a wall defining the device dimensioned for insertion and placement within a nasal passage, with the wall formed of a nasal acceptable microporous material, (b) a reservoir surrounded by the wall and comprised of a solid carrier permeable to drug and containing drug in an amount sufficient for the device to meter it at a continuous and controlled rate for a prolonged period of time from the device, (c) a liquid medium permeable to the passage of drug by diffusion charged in the micropores, and (d) wherein the device releases drug when in a nasal environment by passage of drug from the carrier and through the liquid to the exterior of the device to produce a useful result. The entire disclosure of U.S. Pat. No. 3,948,254 (Zaffaroni) is expressly incorporated herein by reference.

Other publications have also reported that introduction of drugs directly into the paranasal sinuses is effective in the treatment of sinusitis. See, Tarasov, D. I., et al., *Application of Drugs Based on Polymers in the Treatment of Acute and Chronic Maxillary Sinusitis*, Vestn Otorinolaringol. Vol. 6, Pages 45-7 (1978). Also, R. Deutschmann, et al., *A Contribution to the Topical Treatment of [Maxillary] Sinusitis Preliminary Communication*, Stomat. DDR 26 (1976), 585-592 describes the placement of a resorbable drug delivery depot within the maxillary sinus for the purposes of eluting drugs, specifically Chloramphenicol. In this clinical series a water soluable gelatin was used as carrier and was mixed with the drug prior to application and introduced as a mass into the sinus. Since the substance had little mechanical integrity and dissolved in a relatively short timeframe, to achieve a therapeutic effect, the author suggested that it must be instilled every 2 to 3 days. An alternative to gelatin could be a sponge loaded with the therapeutic substance as suggested in U.S. Pat. No. 6,398,758 (Jacobsen, et al.). In this patent directed at delivering a sustained release device against the wall of a blood vessel, a hollow cylindrical sponge is loaded with drug and pressed against the wall. This allows the drug to contact the wall while sustaining blood flow within the center of the lumen. Further, a skin is provided to direct the drug into the walls of the blood vessel and prevent drug from flowing into the lumen. While sponges loaded with drug at the time of their application do permit some degree of sustained release, the time required to load them also correlates closely the time over which they will elute substance. Thus, if delivery is required for a longer period of time additional mechanisms must be employed to regulate their release.

There are also several examples in the patent literature where various sustained release mechanisms have generally been proposed using systems with pre-incorporated drugs into matrices or polymers. These include U.S. Pat. No. 3,948,254 (Zafferoni), US 2003/0185872A2 (now U.S. Pat. No. 7,074,426) (Kochinke), WO 92/15286 (Shikani), and U.S. Pat. No. 5,512,055 (Domb, et al.). In general, these references discuss various materials and structures that may be used to construct sustained drug delivery vehicles and provide a good overview of the state of sustained drug delivery art. While helpful in laying out certain materials and schemes for creating sustained release systems for drugs, each of these references, however, do not describe specific methods, means or structures which would permit them to be easily adapted for intended uses in the targeted in this application.

There remains a need in the art for the development of new devices and methods for delivering drugs and other therapeutic or diagnostic substances into paranasal sinuses or other locations within the body for the treatment of sinusitis or other diseases and disorders.

SUMMARY OF THE INVENTION

In accordance with the present invention, there is provided a method and device for delivering a substance to a location within the body of a human or animal subject (e.g., within the nose, paranasal sinus, ostium of a paranasal sinus, eustachian tube, etc.) to diagnose or treat a disorder (e.g., sinusitis or another disorder of the ear, nose or throat). In general, this method comprises the steps of: A) providing an implantable substance delivery device that comprises i) a substance reservoir that may subsequently be loaded with a substance that is therapeutically effective to diagnose or treat the disorder and ii) a barrier that will limit the rate at which a substance will flow out of the reservoir; B) providing a substance that is useable to diagnose or treat the disorder; C) introducing a quantity of the substance into the reservoir; and D) implanting the device at a location within the subject's body such that the substance will be delivered by the implanted device to a location within the subject's body. In some applications, the physician may load a desired therapeutic or diagnostic substance into the reservoir before the device is implanted in the subject's body. In other applications, the physician may load a desired therapeutic or diagnostic substance into the reservoir after the device has been implanted in the subject's body. The device may be biodegradable or non-biodegradable and may or may not be removed from the body after it has remained implanted for a desired period of time. The barrier of the device may comprise an aperture, membrane (e.g., semi-permeable membrane) or other structure that allows one or more substances having certain key property or properties to pass through the barrier at approximately a known rate. Examples of the key properties that may determine a substance's ability to pass through the barrier at approximately the known rate include but are not limited to viscosity or a range of viscosities, molecular weight or range or molecular weights, osmolarity or range of osmolarities, osmolality or range of osmolalities, electrical charge, presence of a chemical group or atom, hydrophilic or hydrophibic properties, the size and/or shape of molecules, etc. Thus, a physician and/or pharmacist may, in some cases, select a barrier and select or specially formulate a substance that possess a particular key property relative to the selected barrier, such that the substance will be delivered through the barrier at an intended delivery rate.

Further in accordance with the invention the reservoir of the device may comprise a hollow cavity, porous material (e.g., an absorptive polymer foam) or combination thereof. The barrier may comprise a membrane or opening that surrounds, substantially surrounds, partially surrounds or is located next to the reservoir such that substance contained within the reservoir will pass through the barrier at a controlled rate.

Still further in accordance with the invention, the implantable substance delivery device may be configured such that, at least when the reservoir is loaded with the substance, the outer surface of the device will have peaks and valleys such that the peaks are in contact with adjacent tissues or other anatomical structure(s) and the valleys remain spaced away from adjacent tissues or other anatomical structures so as not to interfere with the physiological function of those tissues or other anatomical structures. Such embodiments of the device may be implanted in areas of the nose or paranasal sinuses lined with ciliated mucosal tissue and the surface(s) of the device within the valleys will remain far enough away from the adjacent ciliated mucosa as to not interfere with mucocilliary transport by such tissue. The diameter or cross-sectional configuration of the device may vary along its length or may be shaped in a conical, frustoconical or curvilinear (e.g., hourglass) shape. Also, the device may have region(s) of differing hardness (e.g., durometer), flexural properties (e.g., stiffness or flexibility) or compliance and such properties may change in response to the presence or absence of the therapeutic or diagnostic substance and/or contact or non-contact with body fluids (e.g., mucous) or other conditions present at the intended site of implantation.

Further aspects, details and embodiments of the present invention will be understood by those of skill in the art upon reading the following detailed description of the invention and the accompanying drawings.

DETAILED DESCRIPTION

The following detailed description and the accompanying drawings are intended to describe some, but not necessarily all, examples or embodiments of the invention only. This detailed description and the accompanying drawings do not limit the scope of the invention in any way.

Figure 1:
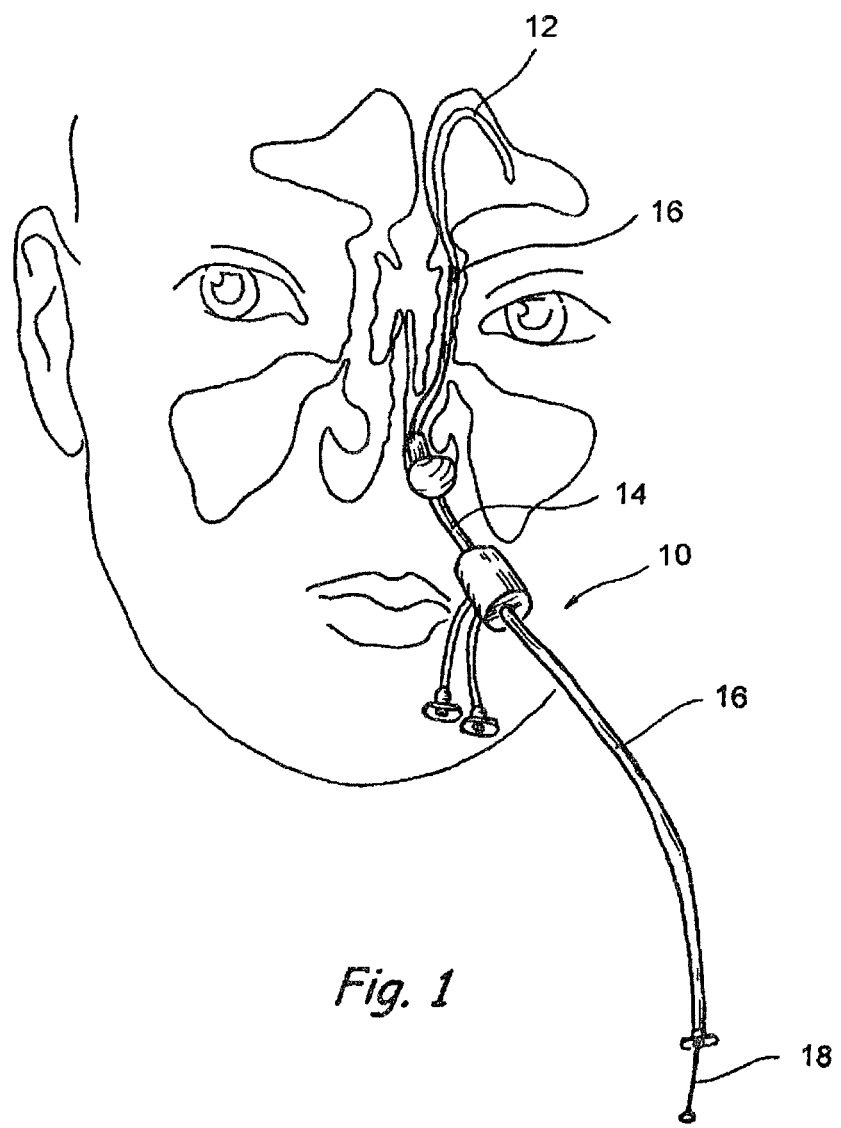
FIG. 1 is a schematic cut-away showing of a human head having a catheter-based substance delivery system of the present invention inserted therein to deliver a substance delivery implant into the left frontal sinus.

The human nose has right and left nostrils or nares which lead into separate right and left nasal cavities. The right and left nasal cavities are separated by the intranasal septum, which is formed substantially of cartilage and bone. Posterior to the intranasal septum, the nasal cavities converge into a single nasopharyngeal cavity. The right and left Eustachian tubes (i.e., auditory tubes) extend from the middle ear on each side of the head to openings located on the lateral aspects of the nasopharynx. The nasopharynx extends inferiorly over the uvula and into the pharynx. As shown in FIG. 1, paranasal sinuses are formed in the facial bones on either side of the face. The paranasal sinuses open, through individual openings or ostia, into the nasal cavities. The paranasal sinuses include frontal sinuses FS, ethmoid sinuses ES, sphenoidal sinuses SS and maxillary sinuses MS.

The present invention provides implantable devices that may be positioned within a naturally occurring or man-made anatomical cavity or passageway such as a nostril, nasal cavity, meatus, ostium, interior of a sinus, etc. to deliver a diagnostic or therapeutic substance to tissues located adjacent to or near the implanted device. Certain non-limiting examples of the present invention are shown in FIGS. 1-12F and described in detail herebelow. Although certain examples shown in these drawings are targeted to the paranasal sinuses and nasal cavities, the devices and methods of the present invention are useable in a wide range of applications in various area of the body, including but not limited to natural or man made orifices and passageways, subcutaneous locations, intravascular or intracardiac locations and locations within the gastrointestinal tract.

The term "diagnostic or therapeutic substance" as used herein is to be broadly construed to include any feasible drugs, prodrugs, proteins, gene therapy preparations, cells, diagnostic agents, contrast or imaging agents, biologicals, etc. Such substances may be in bound or free form, liquid or solid, colloid or other suspension, solution or may be in the form of a gas or other fluid or non-fluid. For example, in some applications where it is desired to treat or prevent a microbial infection, the substance delivered may comprise pharmaceutically acceptable salt or dosage form of an antimicrobial agent (e.g., antibiotic, antiviral, antiparacytic, antifungal, etc.), a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, immunomodulator), etc.

Some nonlimiting examples of antimicrobial agents that may be used in this invention include acyclovir, amantadine, aminoglycosides (e.g., amikacin, gentamicin and tobramycin), amoxicillin, amoxicillin/clavulanate, amphotericin B, ampicillin, ampicillin/sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscarnet, ganciclovir, atifloxacin, imipenem/cilastatin, isoniazid, itraconazole, ketoconazole, metronidazole, nafcillin, nafcillin, nystatin, penicillin, penicillin G, pentamidine, piperacillin/tazobactam, rifampin, quinupristin-dalfopristin, ticarcillin/clavulanate, trimethoprim/sulfamethoxazole, valacyclovir, vancomycin, mafenide, silver sulfadiazine, mupirocin (e.g., Bactroban Nasal®, Glaxo SmithKline, Research Triangle Park, N.C.), nystatin, triamcinolone/nystatin, clotrimazole/betamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulponated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acidform); non-pathogenic or "friendly" microbes that cause the production of hydrogen peroxide or other substances that kill or inhibit the growth of pathogenic microbes (e.g., *lactobacillus*); antimicrobial proteins or peptides such as those described in U.S. Pat. No. 6,716,813 (Lin et al.) which is expressly incorporated herein by reference or antimicrobial metals (e.g., colloidal silver).

Additionally or alternatively, in some applications where it is desired to treat or prevent inflammation the substances delivered in this invention may include various steroids or other anti-inflammatory agents (e.g., nonsteroidal anti-inflammatory agents or NSAIDS), analgesic agents or antipyretic agents. For example, corticosteroids that have previously administered by intranasal administration may be used, such as beclomethasone (Vancenase® or Beconase®), flunisolide (Nasalide®), fluticasone proprionate (Flonase®), triamcinolone acetonide (Nasacort®), budesonide (Rhinocort Aqua®), loterednol etabonate (Locort) and mometasone (Nasonex®). Other salt forms of the aforementioned corticosteroids may also be used. Also, other non-limiting examples of steroids that may be useable in the present invention include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as nimesulide)

Additionally or alternatively, in some applications, such as those where it is desired to treat or prevent an allergic or immune response and/or cellular proliferation, the substances delivered in this invention may include a) various cytokine inhibitors such as humanized anti-cytokine antibodies, anti-cytokine receptor antibodies, recombinant (new cell resulting from genetic recombination) antagonists, or soluble receptors; b) various leucotriene modifiers such as zafirlukast, montelukast and zileuton; c) immunoglobulin E (IgE) inhibitors such as Omalizumab (an anti-IgE monoclonal antibody formerly called rhu Mab-E25) and secretory leukocyte protease inhibitor) and d) SYK Kinase inhibitors such as an agent designated as "R-112" manufactured by Rigel Pharmaceuticals, Inc, or South San Francisco, Calif.

Additionally or alternatively, in some applications, such as those where it is desired to shrink mucosal tissue, cause decongestion or effect hemostasis, the substances delivered in this invention may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered in this invention may include various mucolytics or other agents that modify the viscosity or consistency of mucous or mucoid secretions, including but not limited to acetylcysteine (Mucomyst™, Mucosil™) and guaifenesin.

In one particular embodiment, the substance delivered by this invention comprises a combination of an anti-inflammatory agent (e.g. a steroid or an NSAID) and a mucolytic agent.

Additionally or alternatively, in some applications such as those where it is desired to prevent or deter histamine release, the substances delivered in this invention may include various mast cell stabilizers or drugs which prevent the release of histamine such as cromolyn (e.g., Nasal Chrom®) and nedocromil.

Additionally or alternatively, in some applications such as those where it is desired to prevent or inhibit the effect of histamine, the substances delivered in this invention may include various antihistamines such as azelastine (e.g., Astylin®), diphenhydramine, loratidine, etc.

Additionally or alternatively, in some embodiments such as those where it is desired to dissolve, degrade, cut, break or remodel bone or cartilage, the substances delivered in this invention may include substances that weaken or modify bone and/or cartilage to facilitate other procedures of this invention wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CGN), trypsin, trypsin/EDTA, hyaluronidase, and tosylylsylchloromethane (TLCM).

Additionally or alternatively, in some applications, the substances delivered in this invention may include other classes of substances that are used to treat rhinitis, nasal polyps, nasal inflammation, and other disorders of the ear, nose and throat including but not limited to anti-cholinergic agents that tend to dry up nasal secretions such as ipratropium (Atrovent Nasal®), as well as other agents not listed here.

Additionally or alternatively, in some applications such as those where it is desired to draw fluid from polyps or edematous tissue, the substances delivered in this invention may include locally or topically acting diuretics such as furosemide and/or hyperosmolar agents such as sodium chloride gel or other salt preparations that draw water from tissue or substances that directly or indirectly change the osmolar content of the mucous to cause more water to exit the tissue to shrink the polyps directly at their site.

Additionally or alternatively, in some applications such as those wherein it is desired to treat a tumor or cancerous lesion, the substances delivered in this invention may include anti-tumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, triazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmette-guerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogs/congeners and derivatives of such compounds as well as other antitumor agents not listed here.

Additionally or alternatively, in some applications such as those where it is desired to grow new cells or to modify existing cells, the substances delivered in this invention may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired, cells that participate in or effect mucogenesis or ciliagenesis, etc.

Additionally or alternatively to being combined with a device and/or a substance releasing modality, it may be ideal to position the device in a specific location upstream in the mucous flow path (i.e. frontal sinus or ethmoid cells). This could allow the deposition of fewer drug releasing devices, and permit the "bathing" of all the downstream tissues with the desired drug. This utilization of mucous as a carrier for the drug may be ideal, especially since the concentrations for the drug may be highest in regions where the mucous is retained; whereas non-diseased regions with good mucous flow will be less affected by the drug. This could be particularly useful in chronic sinusitis, or tumors where bringing the concentration of drug higher at those specific sites may have greater therapeutic benefit. In all such cases, local delivery will permit these drugs to have much less systemic impact. Further, it may be ideal to configure the composition of the drug or delivery system such that it maintains a loose affinity to the mucous permitting it to distribute evenly in the flow. Also, in some applications, rather than a drug, a solute such as a salt or other mucous soluble material may be positioned at a location whereby mucous will contact the substance and a quantity of the substance will become dissolved in the mucous thereby changing some property (e.g., pH, osmolarity, etc) of the mucous. In some cases, this technique may be used to render the mucous hyperosmolar so that the flowing mucous will draw water and/or other fluid from polyps, edematous mucosal tissue, etc., thereby providing a drying or desiccating therapeutic effect.

Additionally or alternatively to substances directed towards local delivery to affect changes within the sinus cavity, the nasal cavities provide unique access to the olfactory system and thus the brain. Any of the devices and methods described herein may also be used to deliver substances to the brain or alter the functioning of the olfactory system. Such examples include, the delivery of energy or the deposition of devices and/or substances and/or substance delivering implant(s) to occlude or alter olfactory perception, to suppress appetite or otherwise treat obesity, epilepsy (e.g., barbiturates such as phenobarbital or mephoobarbital; iminostilbenes such as carbamazepine and oxcarbazepine; succinimides such as ethylsuximide; valproic acid; benzodiazepines such as clonazepam, clorazepate, diazepam and lorazepam, gabapentin, lamotrigine, acetazolamide, felbamate, levetiraceam, tiagabine, topiramate, zonisamide, etc.), personality or mental disorders (e.g., antidepressants, antianxiety agents, antipsychotics, etc.), chronic pain, Parkinson's disease (e.g., dopamine receptor agonists such as bromocriptine, pergolide, ropinitrol and pramipexole; dopamine precursors such as levodopa; COMT inhibitors such as tolcapone and entacapone; selegiline; muscarinic receptor antagonists such as trihexyphenidyl, benztropine and diphenhydramine) and Alzheimer's disease, Huntington's disease or other dementias, disorders of cognition or chronic degenerative diseases (e.g. tacrine, donepezil, rivastigmine, galantamine, fluoxetine, carbamazepine, clozapine, clonazepam and proteins or genetic therapies that inhibit the formation of beta-amyloid plaques), etc.

In certain applications, such as those intended for the treatment of sinusitis or other disorders of the ear, nose or throat, the implantable substance delivery devices and methods of the present invention may satisfy one or more of the following objectives:

1. Cleaning of mucous: The implantable substance delivery devices of this invention may be configured such that, when implanted in a nasal or perinasal passageway, they will allow at least a portion of the adjacent anatomical wall(s) to maintain muco-ciliary action. To accomplish this the devices may have discrete areas which contact the adjacent anatomical wall(s) and other areas that do not contact the adjacent anatomical wall(s) and/or they may incorporate an internal hollow lumen. While some embodiments of the invention include a central lumen, in most cases, it may be impossible or impracticable for mucous to flow through the lumen of the implanted device via gravity or sheer pressure. Thus, this central lumen may not be a usable structure to maintain patency of the anatomical passageway since in such cases fluids may more easily be conducted around the device. Accordingly, in other embodiments of the present invention as described herein, the device may comprise spaced apart struts or members which allow mucous to flow there-between, thus avoiding any need for the mucous to enter a lumen or bore within the device. Also, there are other embodiments of the current invention where the struts are relatively thin and the device in composed of an open-cellular structure such that the cilia are allowed to contact the inner lumen of the device directly. In these circumstance the clearing of mucous may be possible through the central lumen without relying on pressure or gravity.

2. Sustained Effect Drug saturated gauze or sponges, as may be used to deliver drugs in some intranasal/intrasinus applications, have little or no ability to regulate the dosage(s) of drug(s) delivered or the dispersion of those drug(s). Further, they may be either non-biodegradable or very quickly biodegradable. At least some embodiments of the devices of the present invention overcome these shortcomings by delivering predetermined dosages of drugs for a predetermined treatment duration and then, after conclusion of the predetermined treatment duration, may be removed or may biodegrade and be eliminated.

3. Minimally Invasive Placement Many of the instruments currently used to perform sinus procedures require significant obliteration of or damage to tissues within the nose or sinus in order to gain access and place implants. However, the devices and methods of the present invention may be carried out with minimal iatrogenic damage to nasal and sinus tissues. Thus, the devices and methods described herein may permit swollen tissues and obstructed lumens to be reduced through the action of the drugs, and for infections to be controlled, thereby resulting in a resolution of symptoms without the need for invasive tissue-damaging therapy such as traditional sinus surgery.

4. Low risk of device infection: In accordance with this invention, implantable substance delivery devices may be made of a material that is naturally antiinfective or may be coated with such a material. This may aid in avoidance of "toxic-shock" syndrome or other similar device related infections. Alternatively they may be removable or resistant to infection as a result of their mechanical structure or integrity.

5. Removable or biodegradable: In some embodiments, the implantable substance delivery devices of the present invention may be biodegradable and/or removable. In some applications, it will be desirable for the device to be biodegradable over a desired time period, yet be removable if conditions merit it's early removal (e.g., before sufficient time has elapsed to allow the device to fully biodegrade). To aid in the removability of the structure a tail, or suture/string attachment point may be provided to permit easy removal in the office.

6. Ability to deliver one or more diagnostic or therapeutic substances: Since sinus disease has many etiologies, it would be ideal to allow the physician to customize the device to contain one or more substances in order to treat an individual patient's disorder. Alternatively, it may also be acceptable to have mixtures or combinations of substances (e.g., a fixed dosage combination of two or more drugs) pre-packaged for loading into the implantable substance delivery device before or after it has been implanted. Such prepackaged mixtures or combinations of substances may be in liquid form suitable for direct loading into the device or may be in dry form (e.g., lyophilized or powder) that may be easily reconstituted with a specified volume of liquid (e.g., sterile water, 0.9% NaCl solution, etc.). Alternatively the device may contain two or more separated chambers that simultaneously or sequentially release drug(s). Alternatively, one other embodiment may include one or more drugs or substances that are pre-bound or pre-loaded within the device without being mixed with any additive or one or more drugs or substances may be added or mixed with other additives at the time of use.

7. Preventing scarring or adhesions: Any material placed in the sinus should be designed of material such that adhesions or scarring may be minimized to allow for the continued patency of the channels in which they are placed. While simply having a mechanical barrier to adhesion may be useful, it is also important that the implant itself does not induce a tissue reaction. Inert materials should be used to avoid this condition. In other embodiments it may be necessary to release an agent capable of preventing the tissue response to the implant. Nominally, although a vast array of therapeutic substances may be used inside the device, it may also have utility simply as a spacer to maintain the passageway in which it is delivered, filled with an inert substance such as saline.

8: Drug delivery kinetics: The devices of the present invention can deliver therapeutic substances in a consistent or predictable manner over the course of the therapy, and if possible, this timing of delivery would be programmable based upon the material chosen. In some circumstances it may be ideal to allow the device to be refilled in situ, but in some embodiments the device may be capable of containing enough therapeutic substance so that refilling would not be necessary. To date there is no device proposed or available which can satisfy these needs and thus the need still exists for new devices and methods for delivering drugs and other therapeutic or diagnostic substances into paranasal sinuses or other locations within the body for the treatment of sinusitis or other diseases and disorders.

Though the implantable substance delivery device may be delivered to or removed from the sinuses or other regions in the ear, nose, or throat via standard surgical techniques, it is of particular interest that the substance delivery device may also be delivered via minimally invasive means which may reduce bleeding, tissue removal, post-operative care, and other surgical issues.

A catheter, which may be malleable, deflectable, and/or have an appropriately shaped body and tip may be introduced into the nose and near or into the location of interest, such as the ostia of a sinus. The catheter may or may not be introduced through an access port located in the nostril. Furthermore, the guide may be positioned in the anatomy via such means, but not limited to: direct visualization, endoscopic imaging, fluoroscopic imaging, electromagnetic sensing, etc. Once properly positioned near or through the appropriate ostium, a guide wire may be advanced through the catheter and into a sinus cavity. For example, in the case of accessing the Maxillary or Frontal sinus, the catheter tip may curve around the uncinate process (without the need to resect the uncinate) and enter through or point toward the appropriate sinus ostia. A guide wire can than be advanced into the sinus cavity. These maneuvers may be done under fluoroscopic, endoscopic, electromagnetic sensing, etc. visualization methods. Appropriately shaped, deflectable, and/or malleable catheters may also be used to gain access to the frontal and sphenoidal sinuses. Once a wire is advanced into the sinus, a balloon catheter may be introduced over the wire in order to enlarge the ostia of the sinus in question if it is deemed necessary. If desired, a second catheter may be advanced over the wire and through the access catheter. This second catheter may be used to exchange for a smaller guide wire—thus allowing for the use of smaller catheters that are compatible with the smaller guide wire.

Access to the Sphenoid sinus may be accomplished similarly by advancing the access catheter medial to the middle turbinate and placing the catheter through or close to the ostium of the sinus. Similar techniques of advancing a guide wire into the sinus with subsequent balloon dilation prior to delivery of the substance delivery device may then follow.

Access to the Ethmoid sinuses may be accomplished similarly by advancing the access catheter into or close to the retrobullar and suprabullar recesses, which provide entry into the ethmoid cells. Similar techniques of navigating and advancing a guide wire through and into the cells with subsequent balloon dilation prior to delivery of the substance delivery device may then follow.

Alternatively, it may be desirable to advance a catheter near the anterior ethmoid (e.g. Ethmoid Bulla) under fluoroscopic, endoscopic, electromagnetic sensing, etc. visualization/navigation. Subsequently, a piercing member such as a needle or catheter may be advance through the access catheter, and through the walls of the anterior and posterior ethmoid cells. Once one or more walls are pierced, a guidewire may be advanced into the ethmoid cells via the needle or other catheter member. Balloon dilation of the pierced anterior and posterior ethmoid cells may be conducted, if desired, prior to placement of the substance delivery device. In general, minimally invasive access to the sinuses and their surrounding areas is a key element to delivering a substance delivery device.

Turning now to FIGS. 1-12F, it is to be understood that such figures show specific examples of the devices and methods of the present invention. Any elements, attributes, components, accessories or features of one embodiment or example shown in these figures may be eliminated from that embodiment or example, or may be included in any other embodiment or example, unless to do so would render the resultant embodiment or example unusable for its intended purpose.

FIG. 1 generally shows a diagram of the head of a human patient wherein a system 10 of the present invention is being employed to implant a substance delivery device 12 of the present invention within the left frontal sinus. As shown, this system 10 comprises a nasal access port device 14, a delivery catheter 16, an elongate member 18 and the implantable substance delivery device 12. The port device 14 is positioned within the nostril, as shown. Examples of nasal port devices that may be useable are described in detail in parent application Ser. No. 10/829,917 (now U.S. Pat. No. 7,654,997) entitled "Devices, Systems and Methods for Diagnosing and Treating Sinusitis and Other Disorders of the Ears, Nose and/or Throat," which is incorporated herein by reference. The catheter 16 is advanced through the port device 14 and through the nasal cavity to a location within or very near the ostium to the left frontal sinus. Prior to or after insertion of the catheter 16, the implantable substance delivery device 12 is loaded into the lumen of the delivery catheter 16 and the elongate member 18 is positioned in the lumen of the delivery catheter 16 proximal to the implantable substance delivery device 12. It will be appreciated that, in some cases, a separate guide catheter (not shown) may be advanced through port device 14 and to a position near the ostium of the left frontal sinus and thereafter the delivery catheter may be advanced through that guide catheter to a position where the distal end of the delivery catheter is in or immediately adjacent to the ostium of the left frontal sinus. Thereafter, the elongate member 18 may be advanced in the distal direction thereby pushing the implantable substance delivery device 12 out of the distal end of the delivery catheter 16. Alternatively, the distal end of the elongate member 18 may be positioned in contact with the proximal end of the drug delivery device 12 within the lumen of the delivery catheter 16 and, thereafter, the elongate member 18 may be held stationary while the delivery catheter 16 is retracted in the proximal direction so as to cause the implantable substance delivery device 12 to pass out of the distal end of the delivery catheter 16. In either case, the substance delivery device 12 will be positioned fully or partially within the frontal sinus and, thereafter, the port device 14, delivery catheter 16 and elongate member 18 may be removed. The implantable substance delivery device 12 may be constructed in various ways, examples of which are shown in FIGS. 2-12F and described herebelow. In any of the embodiments of this invention, the desired diagnostic or therapeutic substance may be loaded into the implantable substance delivery device 12 before and/or after the device 12 has been implanted within the body.

Figure 2:
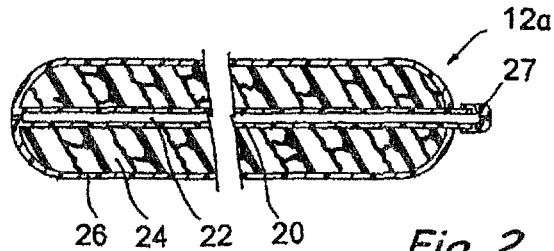
FIG. 2 is a longitudinal sectional view of one embodiment of an implantable substance delivery device of the present invention having a generally round cross-sectional configuration and a self-sealing fill site.
Figure 2A:
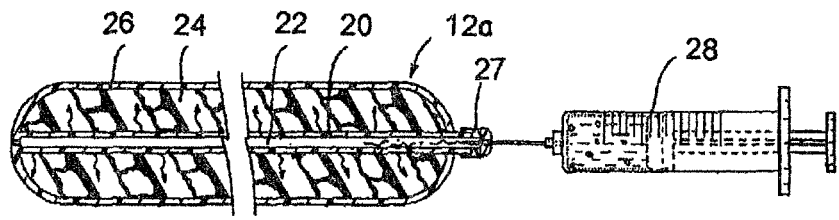
FIG. 2A is a longitudinal sectional view of the device of FIG. 2 as it is being filled with a substance.
Figure 2B:
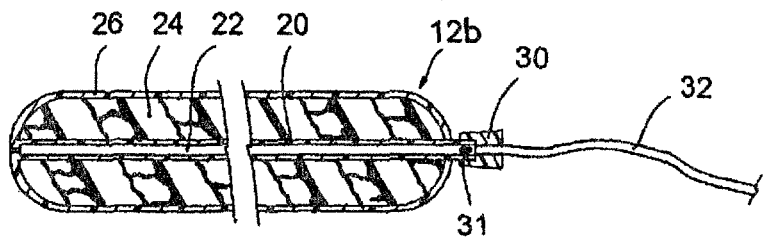
FIG. 2B is a longitudinal sectional view of another embodiment of an implantable substance delivery device of the present invention having a fill tube that extends from its fill site.
Figure 2C:
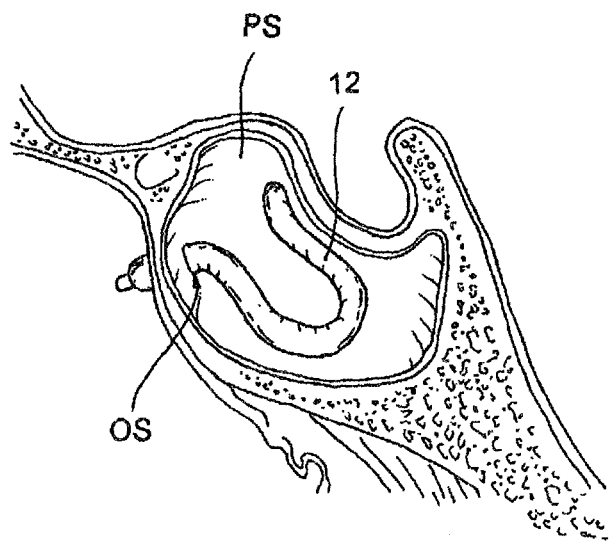
FIG. 2C is a sectional view of a paranasal sinus having an implantable substance delivery device of the present invention implanted therein.

FIGS. 2-2C show one embodiment of an implantable substance delivery device 12a which tube 20 having a lumen 22, a porous matrix 24 and an outer barrier 26. One end of the tube 20 protrudes through the outer barrier 26 and has a needle-penetrable, self-sealing cap 27 thereon. The other end of the tube 20 is closed such that the lumen 22 of the tube forms a hollow cavity within the approximate center of the porous matrix 24. A solution containing the desired therapeutic or diagnostic substance is introduced into the lumen 22 of the tube 20 by a syringe and needle 28, as shown in FIG. 2A. The tube 20 is constructed of porous or permeable material such as expanded polytetrafluoroethylene (ePTFE) or a bioabsorbable material such as porous poly (L-lactic acid) (PLLA) or poly(L-glycolic acid) (PLGA,) etc. which allows the substance to pass through the wall of the tube 20 and into the porous matrix 24. In this manner, the porous matrix 24 becomes substantially saturated or loaded with the substance such that the lumen 22 of tube 20 and the porous matrix 24 combine to form a reservoir in which a quantity of the substance is contained. The porous matrix may be formed of a biodegradable or non-biodegradable porous material such as a flexible or rigid polymer foam, cotton wadding, gauze, hydrogel, collagen etc. Examples of biodegradable polymers that may be foamed or otherwise rendered porous include poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. This device 12a may be fully or partially biodegradable or non-biodegradable. In non-biodegradable embodiments of the device 12a, the tube 20, porous body 24 and outer barrier 26 The tube 20 may be formed of any suitable material, such as various commercially available biocompatible polymers including but not limited to silicone rubber, polyethylene terephthalate, ultra high molecular weight polyethylene, expanded polytetrafloroethylene, polypropylene, polycarbonate urethane, polyurethane, polyamides.

Any embodiment of this invention, such as that shown in FIG. 2-2B, could incorporate a means for assisting the transport of a substance across the barrier. Such a device could take the form of a mechanical pump, an electromechanical pump, a nanotechnology pumping mechanism, or an electrical device that emits a current to drive the transport. This means could be incorporated into the barrier itself or into the porous matrix. A more specific example of a mechanical embodiment would be to mechanically change the reservoir size so that the volume of substance to be delivered is continually under positive pressure to drive its transport across the barrier. This mechanical change could be controlled via micro-electronics and could be pre-programmed or remotely controlled through various wireless communication technologies. Another example of a mechanical means to maintain pressure within the reservoir would be to incorporate a membrane barrier that contracts or shrinks as the drug volume diminishes such as an osmotic pump, or one activated by an internal chemical reaction. This contraction could be achieved by creating the membrane barrier from an elastic or shrinking polymer or by including movable filaments or sections that decrease the reservoir volume.

In any embodiment of this invention, the wall of any tube 22 or other cavity formed within or next to the porous matrix 24 may be constructed of material that controls the rate at which the substance passes from the lumen 22 of the tube 20 into the porous matrix 24. Also, the outer barrier 26 may be constructed of material (e.g., a semi-permeable membrane or film) which will control the rate at which the substance will pass from the porous matrix 24 through the outer barrier 26 and out of the device 12. There may be other embodiments of the substance delivery device that utilize multiple chambers within the device to contain multiple drugs. These chambers could be arranged in various configurations, including, but not limited to being arranged axially so that a strip of each chamber travels the length of the device but the cross-section shows multiple compartments, longitudinally so that the distal portion of the device could contain a different drug than the middle or proximal portions, or in layers (like an onion) such that the first drug that gets delivered may be different than the next drug to treat various afflictions at different times—i.e. first addressing inflammation, then after a predetermined period to begin releasing antimicrobials to combat infection. In the layered configuration, the dividing membranes may or may not be biodegradable. The device 12 of this invention may initially be provided without diagnostic or therapeutic substance contained in the device 12. In such cases, a physician may then select or formulate a particular therapeutic or diagnostic substance or combination of such substances into the device 12 before the device is implanted in the subject's body. In other applications, the physician may load a desired therapeutic or diagnostic substance or combination of such substances into the device 12 after the device has been implanted in the subject's body. To facilitate the physician's selection or formulation of the diagnostic or therapeutic substance(s) to be loaded into the device 12, the device may be accompanied by a data compilation for facilitating dilution of substance(s) and loading of the devices 12 such that desired dosage(s) of the substance(s) that have been loaded into the device 12 will be delivered by the implanted device 12. Such data compilation may be in the form of tabular data, algorithm(s) etc. Also, such data compilation may be provided in written form (e.g., as a table or list) as hard copy (e.g., a package insert or booklet) or stored in electronic form (e.g., on compact disc, accessible from a website, programmed into a computer or microprocessor device such as a hand held electronic dosage calculator that is programmed specifically for use in conjunction with the devices 12 of the present invention). The dosage of particular substance(s) delivered by the devices 12 will be determined rate(s) at which certain substances, preparations, mixtures or concentrations of solutes or substances having certain defined key properties will pass through the barriers 26 of the devices 12. The data compilation may include or comprise examples or lists of certain key properties for which specific barrier transition rates may be provided include a viscosity or a range of viscosities, molecular weight or range of molecular weights, an electrical charge, osmolarity or a range of osmolarities, osmolality or a range of osmolalities, presence of a certain chemical group or atom, relative hydrophilicity and/or hydrophobic properties, etc. An example of one type of data compilation that may be provided to facilitate preparation and loading of a device 12 of the present invention with specific steroid or steroid/antimicrobial formulations is a tabular presentation as shown in Table 1 below:

TABLE 1

| (Drug or Drug Combination/ Solvent) | Concentration of Drug or Drug Combination In Solution (mg of drug or drug Combination per ml of solution) | Diffusion Rate Out of Device (amount of each drug delivered per 24 hour period) |
|---|---|---|
| fluticasone proprionate (as microfine aqueous suspension) | X mg/ml<br>Y mg/ml<br>Z mg/ml | 200 mcg fluticasone proprionate/24 hr<br>230 mcg fluticasone proprionate/24 hr<br>260 mcg fluticasone proprionate/24 hr |
| cefuroxime axetil + fluticasone proprionate in 0.9% saline | X mg/ml<br>Y mg/ml<br>Z mg/ml | 200 mcg fluticasone proprionate + 8 mg cefuroxime axetil/24 hr<br>230 mcg fluticasone proprionate + 12 mg cefuroxime axetil/24 hr<br>260 mcg fluticasone proprionate + 20 mg cefuroxime axetil/24 hr |
| triamcinolone acetonide (as aqueous microcrystalline suspension). | X mg/ml<br>Y mg/ml<br>Z mg/ml | 180 mcg triamcinolone cetonide/24 hr<br>220 mcg triamcinolone cetonide/24 hr<br>260 mcg triamcinolone cetonide/24 hr |
| amoxicillin + clavulanate + triamcinolone acetonide in 0.9% saline as solution/ aqueous microcrystalline suspension | X mg/ml<br>Y mg/ml<br>Z mg/ml | 180 mcg triamcinolone cetonide + 40 mcg amoxicilin + 20 mcg clavulanate/24 hr<br>220 mcg triamcinolone cetonide cetonide + 60 mcg amoxicilin + 40 mcg clavulanate/24 hr<br>260 mcg triamcinolone cetonide cetonide + 80 mcg amoxicilin + 60 mg clavulanate/24 hr |
| clotrimazole + betamethasone dipropionate in polyethylene glycol | X mg/ml<br>Y mg/ml<br>Z mg/ml | 170 mcg clotrimazole + 100 mcg betamethasone dipropionate/24 hr<br>200 mcg clotrimazole + 125 mcg betamethasone dipropionate/24 hr<br>125 mcg clotrimazole + 150 mcg betamethasone dipropionate/24 hr |
| mupirocin calcium | X mg/ml<br>Y mg/ml<br>Z mg/ml | 1 mg mupirocin calcium/24 hr<br>4 mg mupirocin calcium/24 hr<br>8 mg mupirocin calcium/24 hr |
| mupirocin calcium + fluticasone proprionate (as solution/ microfine aqueous suspension) | X mg/ml<br>Y mg/ml<br>Z mg/ml | 1 mg mupirocin calcium + 200 mcg fluticasone proprionate/24 hr<br>4 mg mupirocin calcium + 220 mcg triamcinolone cetonide/24 hr<br>8 mg mupirocin calcium + 260 mcg fluticasone proprionate/24 hr |

All percentages set forth in this table are expressed as percent by weight. It is to be appreciated that this table is merely an illustrative example provided to show one way in which instructional information or data on substance release rates that may accompany certain implantable substance delivery devices 12 of the present invention to facilitate their loading and use with different substances and/or differing concentrations of substances. The actual substances used and actual delivery rates of those substances will depend on the intended use of the device 12, the key properties of the substance to be loaded into the device 12 and the relative porosity or permeability of the porous matrix 24 and/or outer barrier 26 of the device 12. The above-set-forth table shows several examples whereby a physician may use a starting preparation that contains one or more drugs (e.g., the preparations listed in the left column) to prepare different dilutions (e.g., concentrations X, Y or Z listed in the middle column) which will deliver different topical doses of the agents contained in the preparation (e.g., the daily dosages listed in the right column). The starting preparation (e.g., the preparations listed in the left column) may comprise a commercially available pharmaceutical preparation that is approved and/or useable for intranasal administration or topical administration to mucosal tissues elsewhere in the body.

The starting preparation (e.g., the preparations listed in the left column) may be a) packaged and/or provided along with the devices 12 of the present invention, b) obtained by the physician separately from the devices 12 of the present invention and/or c) pre-loaded in concentrated (e.g., dry or lyophilized form) within the devices 12 of the present invention, as described herein. In some cases, the devices 12 may be provided with a dry (e.g, lyophilized or powdered) diagnostic or therapeutic substance (e.g., a drug preparation) contained in the device (e.g. within the lumen 22 of the tube 20 and/or within the porous matrix 24) and the physician may subsequently inject a measured amount of a solvent (e.g., sterile water, 0.9% NaCl solution, basic salt solution, etc.) to reconstitute or dissolve the substance and to expand or activate the device 12. In such cases, the instructions or other information provided with the device 12 may include information for different concentrations of substance produced by injecting different amounts of solvent. In other cases, the devices may be provided in an expanded state and need to be compressed or re-shaped for delivery then re-expanded fully, slightly, or not at all depending upon the desired implantation location. As stated above, in some cases, the starting preparation (e.g., the preparations listed in the left column) may be commercially available preparations. For example, fluticasone proprionate referred to in the first 1, 2 and 7 of Table 1 is commercially available as a preparation for intranasal spray administration as Flonase® nasal spray (Glaxo-SmithKline, Research Triangle Park, N.C.). Fluticasone propionate, the active component of Flonase® nasal spray, is a synthetic corticosteroid having the chemical name S-(fluoromethyl)6 ⟨,9-difluoro-11®-17-dihydroxy-16⟨-methyl-3-oxoandrosta-1,4-diene-17®-carbothioate, 17-propionate. It is provided as an an aqueous suspension of microfine fluticasone propionate containing microcrystalline cellulose and carboxymethylcellulosesodium, dextrose, 0.02% w/w benzalkonium chloride, polysorbate 80, and 0.25% w/wphenylethyl alcohol, and having a pH between 5 and 7. This commercially available Flonase product may, in some cases, serve as the base preparation (left column of Table 1) which may be combined with one or more other substances and/or prepared in various dilutions (e.g., middle column of Table 1) prior to being loaded into the device 12 such that the device 12 will, when subsequently implanted in the subject's body, deliver a desired dosage of fluticasone propionate alone or in combination with other agent(s) (right column of Table 1). In instances such as this where the substance is in the form of a suspension, the suspension may be formulated such that it will remain stable within the implanted device 12 and the barrier 26 of the device 12 may comprise a membrane that has pores which are large enough to allow the particles (e.g., microparticles) of the suspension to pass through the barrier at the desired rate.

Similarly, triamcinolone acetonide referred to in rows 3 and 4 of Table 1 is commercially available as Nasacort® AQ nasal spray (Aventis Pharmaceuticals, Inc., Bridgewater, N.J.). Triamcinolone acetonide, the active ingredient in Nasacort® AQ nasal spray, is 9-Fluoro-11β,16α,17,21-tetrahydroxypregna-1,4-diene-3,20-dione cyclic 16,17-acetal with acetone ($C_{24}H_{31}FO_6$). It is provided as a microcrystalline suspension of triamcinolone acetonide in an aqueous medium with microcrystalline cellulose, carboxymethylcellulose sodium, polysorbate 80, dextrose, benzalkonium chloride, and edetate disodium. Hydrochloric acid or sodium hydroxide may be added to adjust the pH to a target of 5.0 within a range of 4.5 and 6.0.

Also, preparations of the antifungal agent clotrimazole combined with the corticosteroid betamethasone dipropionate as referred to in row 5 of Table 1 are commercially available as Lotrisone® lotion (Schering Corporation, Kenilworth, N.J.) for topical application to treat fungal infections. Chemicaliy, clotrimazole is 1-(a-Chloro,a,a-diphenylbenzyl) imid-azole, with the empirical formula $C_{22}H_{17}ClN_2$ and a molecular weight of 344.8. Clotrimazole is an odorless, white crystalline powder, insoluble in water and soluble in ethanol. Betamethasone dipropionate has the chemical name 9-Fluoro-1,16,17,21-trihydroxy-16B-methylpregna-1,4-diene-3,20-dione-17,21-dipropionate, with the empirical formula $C_{28}H_{37}FO_7$ and a molecular weight of 504.6. Betamethasone dipropionate is a white to creamy white, odorless crystalline powder, insoluble in water. Each gram of Lotrisone® lotion contains 10 mg clotrimazole and 0.643 mg betamethasone dipropionate (equivalent to 0.5 mg betamethasone), in a hydrophilic base of purified water, mineral oil, white petrolatum, cetyl alcohol plus stearyl alcohol, ceteareth-30, propylene glycol, sodium phosphate monobasic monohydrate, and phosphoric acid; benzyl alcohol as a preservative. For applications where the device 12 of the present invention is to be implanted in the nose, paranasal sinus or other location within the ear, nose or throat, the base preparation (left column of Table 1) may comprise low-viscosity forms of the Lotrisone® lotion or may comprise a solution or suspension of microparticles containing the active ingredients of Lotrisone® lotion absent the lotion base (e.g, excluding some or all of the mineral oil, white petrolatum, cetyl alcohol plus stearyl alcohol, ceteareth-30 and/or propylene glycol).

Also, mupirocin calcium is an antibiotic that is commercially available as Bactroban Nasal® ointment (GlaxoSmithKline, Research Triangle Park, N.C.) for intranasal application. Bactroban Nasal® ointment contains 2.15% w/w mupirocin calcium (equivalent to 2.0% pure mupirocin free acid) in a soft white ointment base that contains paraffin and a mixture of glycerin esters (Softisan® 649). The Mupirocin calcium is in the form of the dihydrate crystalline calcium hemi-salt of mupirocin. Chemically, it is (αE,2S,3R,4R,5S)-5-[(2S,3S,4S,5S)-2,3-Epoxy-5-hydroxy-4-methylhexyl]tetrahydro-3,4-dihydroxy-β-methyl-2H-pyran-2-crotonic acid, ester with 9-hydroxynonanoic acid, calcium salt (2:1), dihydrate. The molecular formula of mupirocin calcium is (C26H43O9)2Ca.2H2O, and the molecular weight is 1075.3. The molecular weight of mupirocin free acid is 500.6. For applications where the device 12 of the present invention is to be implanted in the nose, paranasal sinus or other location within the ear, nose or throat, the base preparation (left column of Table 1) may comprise low-viscosity forms of the Bactroban Nasal® ointment or may comprise a solution or suspension of microparticles containing the active ingredients of Bactroban Nasal® ointment absent the ointment base (e.g, excluding some or all of the paraffin andor glycerin esters (Softisan® 649)).

FIG. 2B shows a variant of the implantable substance delivery device 12b comprising the same components as the device 12a of FIGS. 2 and 2A but, instead of the needle-penetrable, self-sealing cap 27, this device 12b has a fill tube 32 connected to the exposed end of the inner tube 22 by way of a removable connector 30. A check valve 31 may be positioned in the lumen 22 just inside of the connector 30. This check valve may be a device or may simply be the function resulting from the elasticity of the materials chosen for its construction. A syringe or other substance injecting or infusing apparatus may be connected to the free end of the fill tube 32 and a diagnostic or therapeutic substance comprising or consisting of a fluid may be introduced through the fill tube 32, through check valve 31 and into the reservoir (i.e., in this embodiment the "reservoir" includes the lumen 22 as well as the adjacent porous matrix 24). Thereafter, the connector cap 30 and fill tube 32 may be removed. Check valve 31 will prevent the substance from backflowing out of the protruding end of the inner tube 20. Alternatively, the fill tube 32 may remain connected to the device 12 and may be closed (e.g., compressed, clamped, clipped, sealed, cut, doubled over, ligated or otherwise manipulated or sealed as shown in the examples of FIGS. 8A-8E and described herebelow).

The outer barrier controls the rate at which the diagnostic or therapeutic substance will diffuse or pass out of the device 12a or 12b. In some applications of the invention, the device 12a or 12b may be provided to a physician in an empty state (i.e., without diagnostic or therapeutic substance contained in lumen 22 or porous matrix 24). The physician may then select or self-formulate one or more diagnostic or therapeutic substances to be loaded into the device 12a, 12b before or after the device 12a, 12b has been implanted in the body.

FIG. 2C shows a general example where this implantable substance delivery device 12, 12a, 12b is implanted within the ostium OS of a paranasal sinus PS such that a portion of the device 12, 12a, 12b extends into the paranasal sinus PS. In such cases where the device 12, 12a or 12b is implanted in a paranasal sinus PS to treat sinusitis, the physician may load the lumen 22 and porous matrix 24 with any drugs or other diagnostic or therapeutic substance that he or she deems suitable for treatment of the condition. For example, the device 12, 12a, 12b may be loaded with a corticosteroid, such as one or more of those corticosteroids listed hereabove that have been approved for intranasal use (e.g., approved for topical application as a nasal spray or for intramucosal injection directly into the nasal turbinates or nasal mucosa). One specific example is an aqueous solution of Fluticasone Proprionate (Flonase, Glaxo-SmithKline). For intranasal or paranasal applications, the empty device 12b shown in FIG. 2A may be initially delivered and positioned within the paranasal sinus PS and the fill tube 32 may extend into the nasal cavity or out of the subjects nostril. The physician may then infuse the desired substance through the fill tube 32 and into the device 12b. After the lumen 22 and porous matrix 24 have been loaded with the desired amount of substance, the connector 30 may be disconnected and the fill tube 32 removed or, alternatively, the fill tube may be allowed to remain attached to the device 12b to facilitation subsequent in situ refilling of the device 12b. In one embodiment, the fill tube is connected to a subcutaneous substance reservoir. The subcutaneous substance reservoir may comprise a pumping mechanism and is especially useful for chronic delivery of the substance. The subcutaneous drug reservoir may be refillable.

Figure 3:
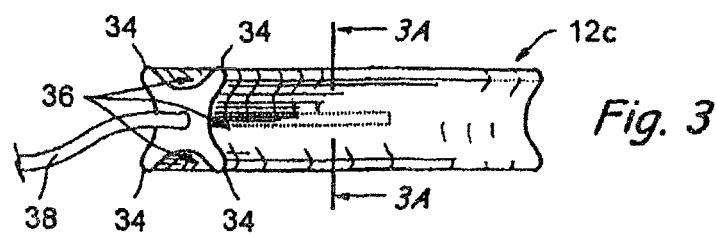
FIG. 3 is a perspective view of another embodiment of an implantable substance delivery device of the present invention having a cross-sectional configuration that provides discrete projections that contact the surrounding anatomical structure(s) while space remains between the remainder of the device and the surrounding anatomical structure(s).
Figure 3A:
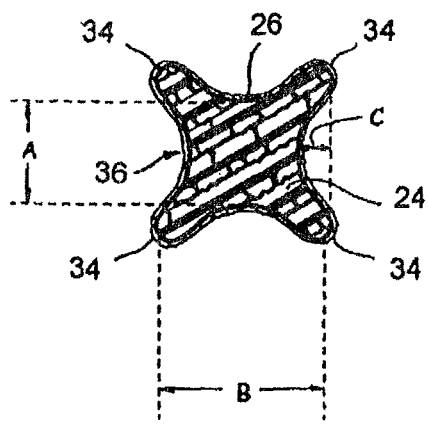
FIG. 3A is a cross sectional view through line 3A-3A of FIG. 3.
Figure 4:
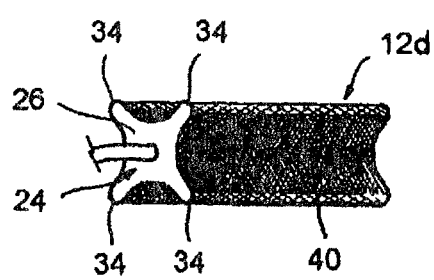
FIG. 4 is a perspective view of another embodiment of an implantable substance delivery device of the present invention having a frame, a porous core, an outer barrier layer and a cross-sectional configuration that provides for discrete areas of contact between the implanted substance delivery device and the surrounding anatomical structure(s).
Figure 4A:
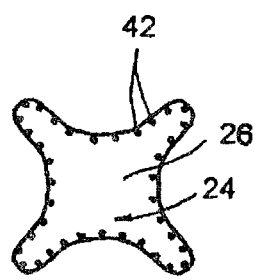
FIG. 4A is an end view of the device of FIG. 4.
Figure 4B:
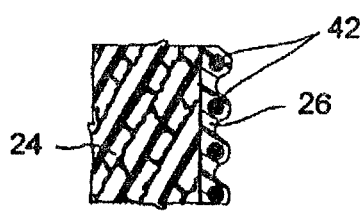
FIG. 4B is a partial cross sectional view of an implantable substance delivery device having a frame, a porous core and an outer barrier layer, wherein the porous core is disposed within the frame and the barrier layer is subsequently applied over the frame.
Figure 4C:
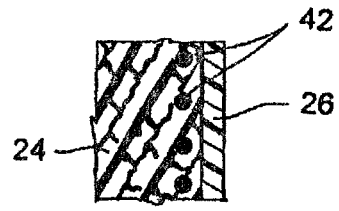
FIG. 4C is a partial cross sectional view of an implantable substance delivery device having a frame, a porous core and an outer barrier layer, wherein the frame is integral of the porous core and the barrier layer is disposed on the outer surface of the porous core.

FIGS. 3-4C show additional embodiments of implantable substance delivery devices 12c and 12d. Like the embodiments 12a and 12b shown in FIGS. 2-2c, these embodiments 12c, 12d comprise at least a porous matrix 24 and an outer barrier 26, as described above. Optionally, these embodiments 12c, 12d may also have an inner tube 20 or other hollow cavity formed within or next to the porous matrix 24. The outer surfaces of these devices 12c, 12d are shaped to define peaks 34 and valleys 36. When the device 12c, 12d is implanted in the body of a subject and loaded with the desired diagnostic or therapeutic substance, the peaks 34 will contact adjacent anatomical tissue and valleys 36 will remain a spaced distance away from adjacent anatomical tissue. In this manner, the surface to surface contact of the device is minimized and normal flow of body fluids and/or function of anatomical tissues may continue in the areas adjacent to the valleys 36 of the device 12c, 12d. For example, in cases where the device 12c, 12d is placed within a nasal cavity, paranasal sinus, Eustachian tube, nasolacrimal duct or other passageway lined with ciliated mucosa, the peaks 34 will make firm abutting contact the mucosal tissue thereby holding the device 12c, 12d in place but the valleys 36 will remain a spaced distance away from the mucosal tissue so as not to substantially interfere with mucocillary transport by that tissue or mucous flow past the implanted device 12c, 12d.

In the examples of FIGS. 3 and 4, the implantable substance delivery devices 12c, 12d have a fill tube 38 that is connected to the device 12c, 12d. In embodiments where there is no hollow cavity or tube 20 within the porous matrix 24, the diagnostic or therapeutic substance may be infused through the tube 38 such that it will be absorbed into porous matrix 24 and no closure or the tube or check valve will then be required as the substance will substantially remain within the porous matrix 24. However, in embodiments where the device 12c, 12d does have a hollow cavity (e.g., a tube 20 as shown in FIGS. 2-2B) within or next to the porous matrix 24, there may be a check valve or other means for closing the tube 38 (e.g., compressing, clamping, clipping, sealing, cutting, doubling over, ligating or otherwise manipulating or sealing the tube as shown in the examples of FIGS. 8A-8E and described herebelow) to prevent the substance from backflowing from the hollow cavity through the tube 38.

FIGS. 4-4C show an embodiment of the implantable substance delivery device 12d that further comprises a frame 40. Such frame may impart structural rigidity or a specific shape to all or any portion of the device 12d. Alternatively or additionally, such frame may act as a scaffold or support structure and/or may be self-expanding or pressure-expandable so as to exert outwardly directed force against an adjacent anatomical tissue or structure. Although FIG. 4 shows a frame 40 that extends over the entire length of the device 12d, it is to be appreciated that the frame 40 may be confined to one or more specific region(s) of any device 12, such as in the example of FIGS. 12D-12E described herebelow. The frame 40 may be formed of any suitable material, including but not limited to wire, mesh, polymer, etc. In the particular example shown in FIGS. 4-4B, the frame 40 comprises a self-expanding stent formed of wire members 42. In some embodiments, the wire members 42 may be positioned on the outer surface of the porous matrix 24 within or inside of the outer barrier 26, as shown in FIG. 4BA. Such embodiments may be manufactured by initially placing the porous matrix 24 (e.g. a sponge or mass of absorptive material) within the frame 40 and then dipping, spray-applying, applying by lay-up of a film or otherwise applying a polymer to from the outer barrier 26 encapsulating the porous matrix 24 and the frame 40, as shown in FIG. 4B. Alternatively, such embodiments may be manufactured by forming (e.g., foaming in place) the porous matrix 24 about the frame 40 such that some or all of the frame members 42 are embedded within the porous matrix 24 as shown in FIG. 4C. The outer barrier 26 may then be placed or formed (e.g., dip coated, sprayed on, applied by lay-up of a film, etc.) on the outer surface of the porous matrix 24 as further shown in FIG. 4C. Also, another method of forming the device may include the initial creation of the barrier film within a mold cavity, and subsequently forming the foam within the film covered mold cavity.

In one embodiment, the device 12d comprises multiple, substantially non-intersecting ridges on its outer surface. The ridges enable only a portion of the device 12d to contact adjacent anatomical tissue while keeping bulk of the device 12d spaced a distance away from adjacent anatomical tissue. The ridges are designed to be substantially parallel to the direction of flow of fluids (e.g. mucous) along the walls of the adjacent anatomical tissue. This design enables reduced interfere with mucocilliary transport by that tissue or the flow of fluids (e.g. mucous) past the device 12d.

Figure 5:
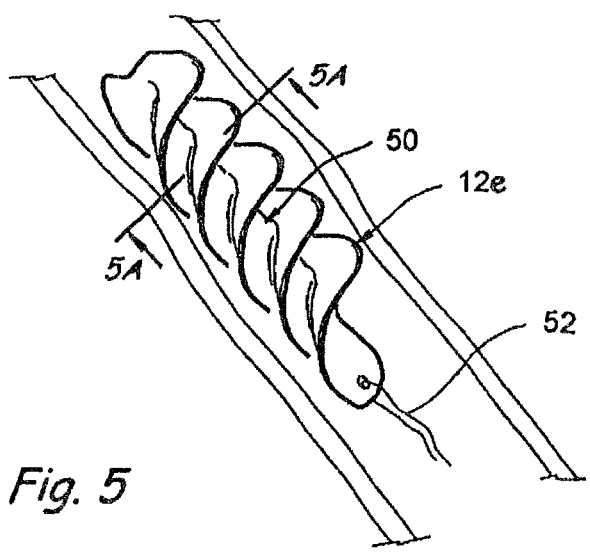
FIG. 5 is a perspective view of a screw-shaped substance delivery device of the present invention positioned within an anatomical passageway.
Figure 5A:
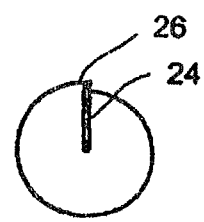
FIG. 5A is a cross sectional view through line 5A-5A of FIG. 5.

Some embodiments of the implantable substance delivery devices 12 of the present invention may be configured to define at lest one lumen of flow channel through which body fluid or extraneously introduced fluid may flow after the device 12 has been implanted in a natural or man made passageway of the body. Examples of this concept include devices 12c, 12d having peaks 34 and valleys 36 as shown in FIGS. 3 and 4, as well as 12e and 12f having other flow-facilitating configurations, examples of which are shown in FIGS. 5-6. The device 12e of FIGS. 5 and 5A comprises a porous matrix 24 covered with an outer barrier 26 and is in the shape of a helical strip (e.g., the shape of a screw or auger). When loaded with the desired diagnostic or therapeutic substance and implanted in a body lumen or passageway, this device 12e defines a helical groove or flowpath 50 through which fluid (e.g., mucous, body fluid, etc.) may flow. The device 12e of FIG. 5 also incorporates an optional grasping member 52 to facilitate grasping of the device 12e by forceps, by hand or by other instruments while removing, moving or manipulating the device 12e. In the particular example shown, the grasping member 52 comprises a strand of suture thread that extends from one end of the device 52 but it is to be appreciated that such grasping member 52 may be of any suitable design or construction and may be located over the entire length of the device. For example, small threads or projections, a net or other graspable structure may be located at numerous location on the outer surface of the device so as to facilitate moving or removing the entire device or portion(s) of the device after the device has begun to break apart or biodegrade in situ.

Figure 6A:
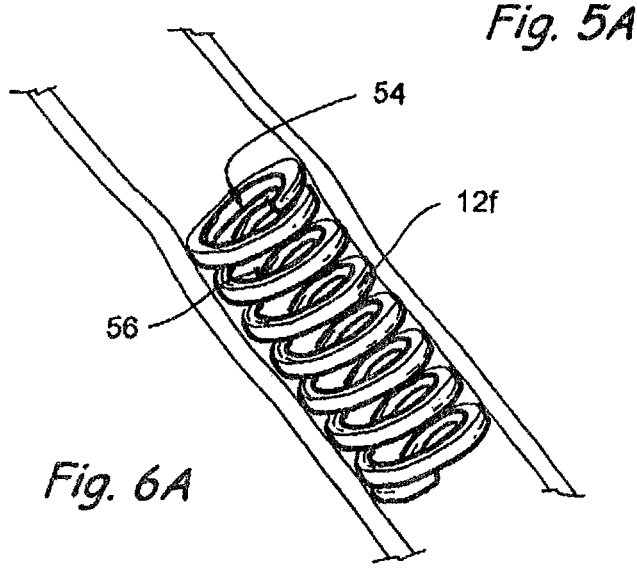
FIG. 6A is a perspective view of a helical substance delivery device of the present invention positioned within an anatomical passageway.

FIG. 6A shows an implantable substance delivery device 12f of the present invention that comprises a helical substance eluting filament. This helical structure defines a hollow lumen 54 through the center of the device 12f and open spaces 56 between individual convolutions of the helix, through which fluids (e.g., mucous or other body fluids) may flow. This helical filament may be formed of any suitable biodegradable or nonbiodegradable material. Examples of biodegradable polymers that may be used to form the filament include include poly(L-lactic acid) (PLLA), poly(L-glycolic acid) (PLGA), polyglycolide, poly-L-lactide, poly-D-lactide, poly (amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. This filament may contain or may be coated with the diagnostic or therapeutic substance or a preparation that contains the diagnostic or therapeutic substance such that the substance will elute from the filament after the filament has been implanted in the body.

Figure 6B:
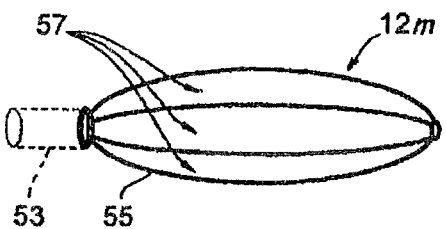
FIG. 6B is a perspective view of another embodiment of a substance delivery device of the present invention comprising a plurality of substantially parallel substance eluting strut members.
Figure 6C:
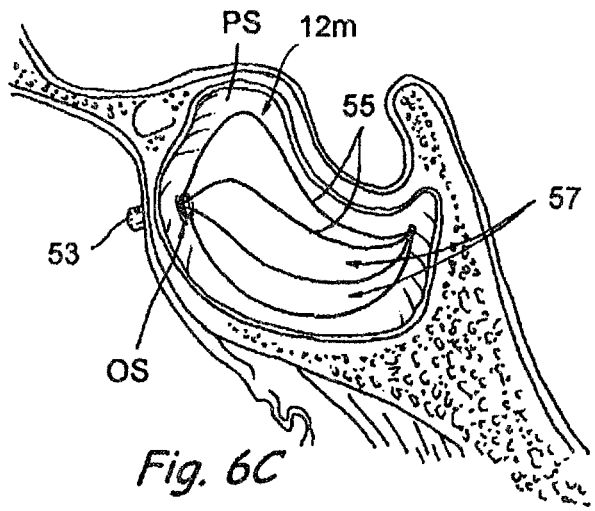
FIG. 6C is a schematic diagram showing the device of FIG. 6B implanted within a paranasal sinus.
Figure 6D:
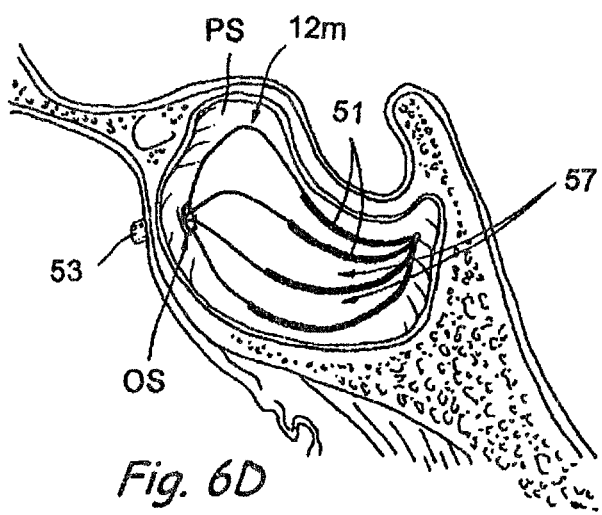
FIG. 6D is a schematic diagram showing a modified version of the device of FIG. 6B implanted within a paranasal sinus.

FIGS. 6B-6D show In another embodiment of an implantable substance delivering device 12m which comprises a plurality of substance eluting struts 55 and may optionally include a spacing member 53. When the device 12m is implanted, such as in the examples of FIGS. 6C and 6D, the struts 55 may be substantially parallel to the direction of flow of fluids (e.g. mucous) along the walls of the adjacent anatomical tissue (e.g., a paranasal sinus, sinus ostium, intranasal meatus, etc.) This design enables reduced interference with the transport of fluids (e.g. mucocilliary transport) along the walls of the adjacent anatomical tissue and in the spaces 57 between the struts 55. The device 12m can be placed both in anatomical cavities (e.g. nasal sinus cavities) and in anatomical passages (e.g. trachea, blood vessels etc.). The device 12m has a configuration that enables the struts 55 to substantially come into direct contact with the flow of fluids (e.g. mucous) past the stent. The device 12m may be delivered to the intended implantation site while in a collapsed configuration and may subsequently expand to an expanded configuration, as shown in the figures. This device 12m may be self expanding or pressure expandable (e.g., by inflation of a balloon within the collapsed device). The thickness of the struts 55 may vary along the length of the device 12m as shown in the example of FIG. 6D. In such embodiments, the diagnostic or therapeutic substance may be contained in and eluted from the thicker in regions 51 of the struts 55 and such substance may subsequently be carried or distributed by a natural flow of body fluid (e.g., mucus flow out of the paranasal sinus). Also, in such embodiments, the thinner regions of the struts 55 may be located near the drainage openings of the anatomical tissue (e.g. ostia of a nasal sinus) to minimize obstruction to fluid drainage. The device 12m may comprise a spacing member 53, such as a tubular or cylindrical hub, and such spacing member 53 may be positionable in an opening of the anatomical tissue (e.g. ostium of a nasal sinus as shown in FIG. 6D). The spacing member 53 may or may not have drug eluting properties. The spacing member 53 may be configured to perform a scaffolding function such as to deter narrowing of a man made or natural an anatomical opening or passage in which it is positioned to ensure that fluid flow through the opening is not compromised. The device 12m may be biodegradable or bioabsorbable.

Figure 7:
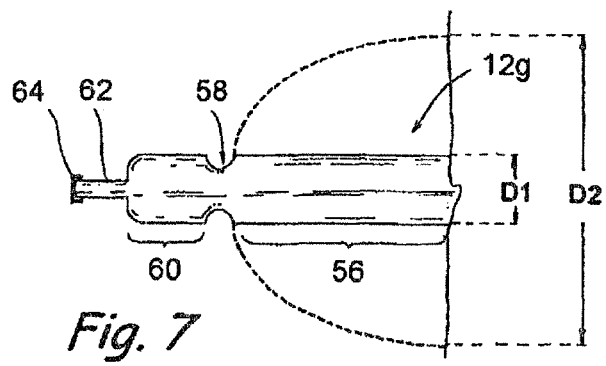
FIG. 7 is a side view of a substance delivery device of the present invention that is configured for implantation and retention within a paranasal sinus.
Figure 7A:
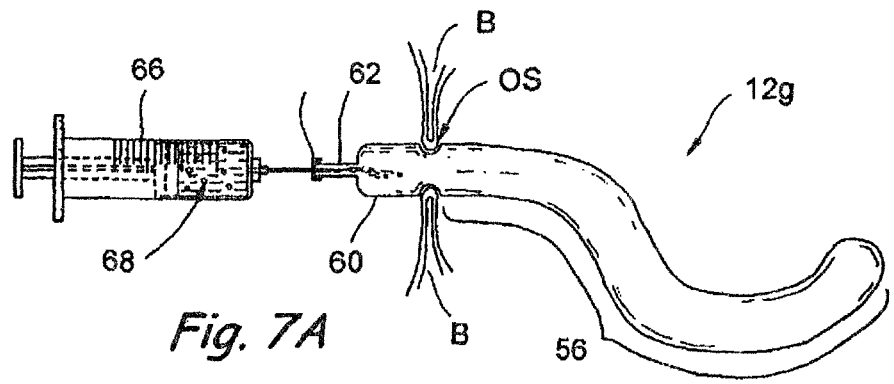
FIG. 7A shows the substance delivery device of FIG. 7 after it has been positioned within a paranasal sinus but before being loaded with therapeutic or diagnostic substance.
Figure 7B:
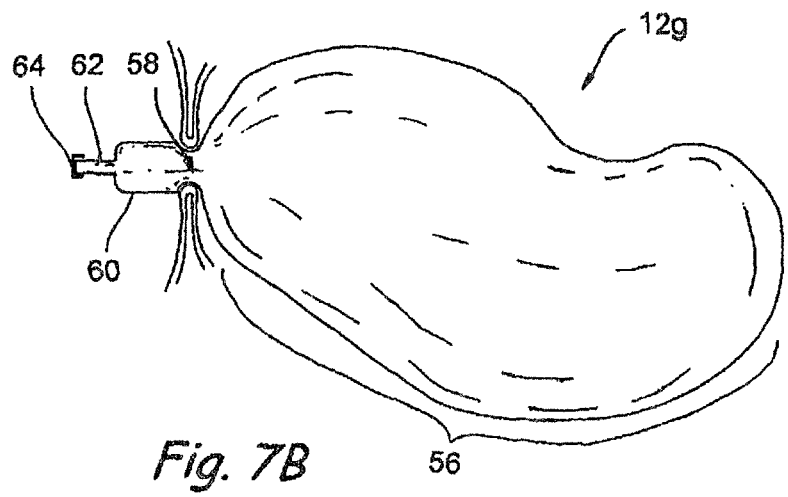
FIG. 7B shows the substance delivery device of FIG. 7 after it has been positioned within a paranasal sinus and after it has been loaded with therapeutic or diagnostic substance.

FIGS. 7-78 show an example of an implantable substance delivery device 12g of the present invention that is designed to be implanted and subsequently retained within a paranasal sinus. This device 12g may include the inner tube 20, porous matrix 24 and outer barrier 26 as shown in FIGS. 2 and 2A and described above. Additionally, this embodiment of the device 12g has an intrasinus portion 56 intended to be positioned within the paranasal sinus, an intraostial portion 58 intended to be positioned within the sinus ostium OS and an intranasal portion 60 intended to protrude into the nasal cavity. A fill tube 62 having a needle-penetrable, self-sealing cap 64 is positioned on the end of the fill tube. It will be appreciated from the foregoing discussion, however, that various other fill site/closure apparatus or designs may be used in place of this fill tube and cap arrangement 62, 64. The intraostial portion 58 of device 12g has an annular groove formed therein. As may be appreciated from FIGS. 7A and 7B this annular groove is configured to receive the annulus of the ostium OS and frictionally engage the underlying bone B, thereby helping to position or seat and/or hold the device 12g in its intended implantation position. Initially, the device 12g is in a collapsed configuration wherein the device has a diameter or maximum cross dimension D1 that is small enough to be advanced through the ostium OS and into the paranasal sinus, as shown in FIGS. 7 and 7A Thereafter, a syringe and needle 66 are used to inject a known volume of a solution containing the desired diagnostic or therapeutic substance 68 into the device 12g. The loading of the substance containing solution into the device 12g causes the intrasinus portion 56 to swell to a larger diameter D2, which is too large to pass through the ostium OS, thereby tending to retain the intrasinus portion 56 within the paranasal sinus, as shown in FIG. 7B.

FIGS. 8A-8E show several non-limiting examples of the manner in which the implantable substance delivery devices 12 of this invention may be sealed or closed to prevent substantial backflow of the diagnostic or therapeutic substance from the device 12 after the device 12 has been loaded with substance.

Figure 8A:
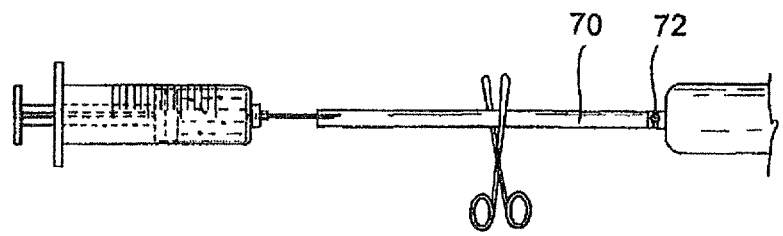
FIG. 8A shows a fill tube for a substance delivery implant device of the present invention having a fill tube with a valve for preventing the substance from back-flowing out of the fill tube.

In the embodiment of FIG. 8A, the device has a long fill tube 70 and a one way check valve 72 within the neck of the fill tube, immediately adjacent to the body of the device. After the device has been implanted and the substance has been infused through the fill tube into the device, the fill tube 70 may be cut to a desired length such that it will not protrude from the subject's body or interfere with the subject's daily activities.

Figure 8B:
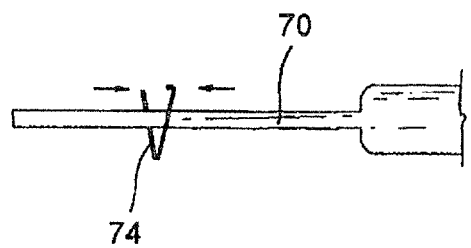
FIG. 8B shows a substance delivery implant device of the present invention having a fill tube with a clip for preventing the substance from back-flowing out of the fill tube.

FIG. 8B shows a device that has a fill tube 70 and a clip 74 which is useable to clip the fill tube 70 to prevent substance from backflowing out of the fill tube 70.

Figure 8C:
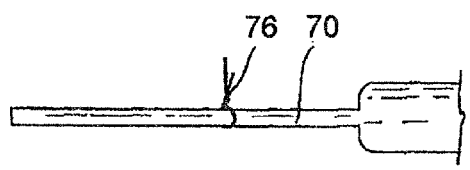
FIG. 8C shows a substance delivery implant device of the present invention having a fill tube with a ligature for preventing the substance from back-flowing out of the fill tube.

FIG. 8C shows a device that has a fill tube 70 and a ligature 76, such as a length of suture material or draw string which is useable to ligate the fill tube 70 to prevent substance from backflowing out of the fill tube 70. An annular indentation or groove may optionally be formed in the fill tube to receive and prevent longitudinal slippage of the ligature 76.

Figure 8D:
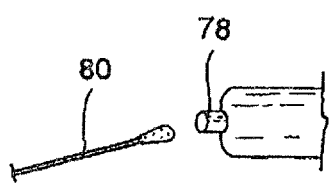
FIG. 8D shows a substance delivery implant device of the present invention having a fill port with an adhesive applicator for applying adhesive to plug the fill port thereby preventing the substance from back-flowing out of the fill port.

FIG. 8D shows a device that has a fill port 78 through which the substance is injected or otherwise loaded into device and an adhesive applicator 80 that may be used to apply an adhesive to the fill port 78 thereby sealing the fill port 78 such that substance will not backflow out of the fill port 78.

Figure 8E:
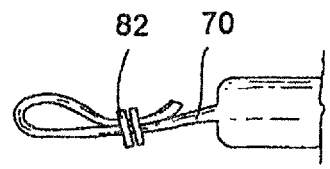
FIG. 8E shows a substance delivery implant device of the present invention having a fill tube that is doubled over and clipped to prevent the substance from back-flowing out of the fill tube.

FIG. 8E shows a device that has a fill tube 70 that is doubled over and a clamp 82 that is useable to clamp the doubled over fill tube 70 to prevent substance from backflowing out of the fill tube 70.

Figure 9:
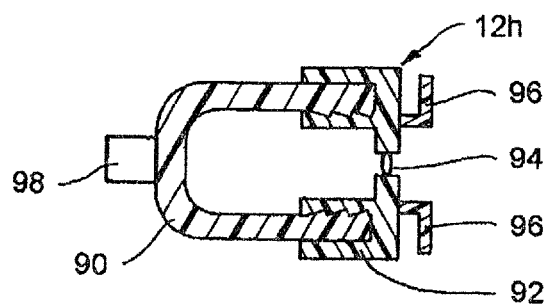
FIG. 9 is a longitudinal sectional view of another embodiment of an implantable substance delivery device according to the present invention.
Figure 9A:
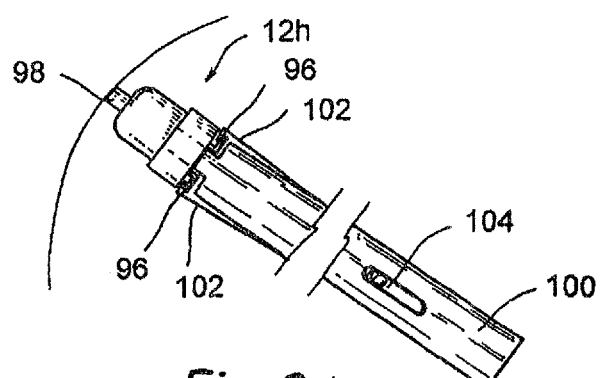
FIG. 9A is a perspective view of a system comprising the implantable substance delivery device of FIG. 9 in combination with a delivery catheter device that is useable for implantation of the implantable substance delivery device within the body of a human or animal subject.
Figure 9B:
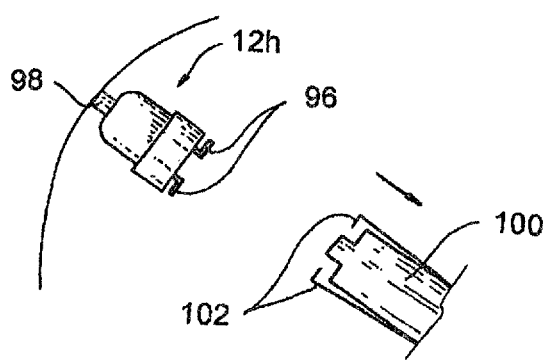
FIG. 9B shows the system of FIG. 9A after the delivery catheter device has been detached from the implanted substance delivery device.

FIGS. 9-9B are directed to another embodiment of an implantable substance delivery device 12h of the present invention. This device 12h comprises a container portion which comprises a container body 90 and a lid 92. The interior of the container portion is loaded with a desired diagnostic or therapeutic substance. The lid 92 has a permeable barrier 94 which allows the diagnostic or therapeutic substance to pass through the barrier 94 at approximately a known rate as described hereabove. An attachment portion 98 attaches the container portion to bone and/or soft tissue. Such attachment portion 98 may comprise any suitable type of attachment apparatus or substance such as an adhesive, barb(s), a screw, a suture or stitch, a clip, a suction apparatus, a stent, a self-expanding portion that grip the walls of the anatomical target etc. As shown in FIG. 9A, the device 12h may be mounted on a delivery catheter 100 which is useable to deliver the device 12h to its intended implantation location. In the example shown, the delivery catheter 100 has engagement members 102 that engage projections 96, 98 on the device 12h, as shown, to hold the device 12h on the end of the delivery catheter as it is advanced into the body to the desired implantation location. The proximal end of the delivery catheter 100 comprises a handpiece having a control knob 104. When the control knob 104 is retracted, the engagement members 102 will disengage the projections 96, 98, thereby releasing the device 12h and allowing the delivery catheter 100 to be retracted and removed as shown in FIG. 9B. In cases where the attachment portion 98 comprises a screw, the delivery catheter 100 may be braided or otherwise constructed in accordance with techniques well known in the art such that the catheter may be rotated to screw the screw into adjacent soft tissue or bone, before the device 12h is released from the delivery catheter 100. As in other embodiments discussed above, the substance may be loaded into this device 12h before or after the device 12h has been implanted within the subject's body.

In one embodiment, the device 12h is implanted in an anatomical location having a mucous flow in such a way that the eluted drug is distributed to a wider region by the mucous flow. This is especially helpful in the enhancing the efficacy of agents like mucolytics as they would accumulate at higher concentrations in regions of higher mucous density. This also enables the reduction in size of the substance delivery mechanism since it can be limited to deliver substances only to particular regions from where the drug can be distributed most efficiently.

Figure 10A:
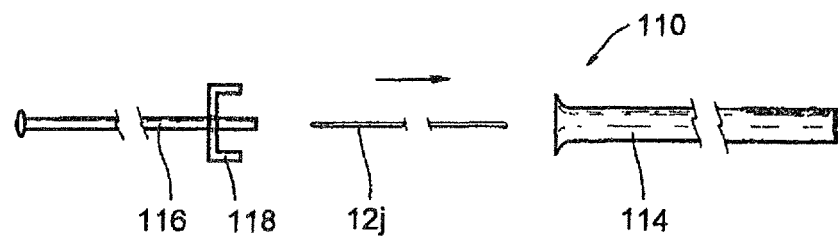
FIG. 10A is an exploded view of a system for delivery and implantation of a substance eluting filament in accordance with the present invention.
Figure 10B:
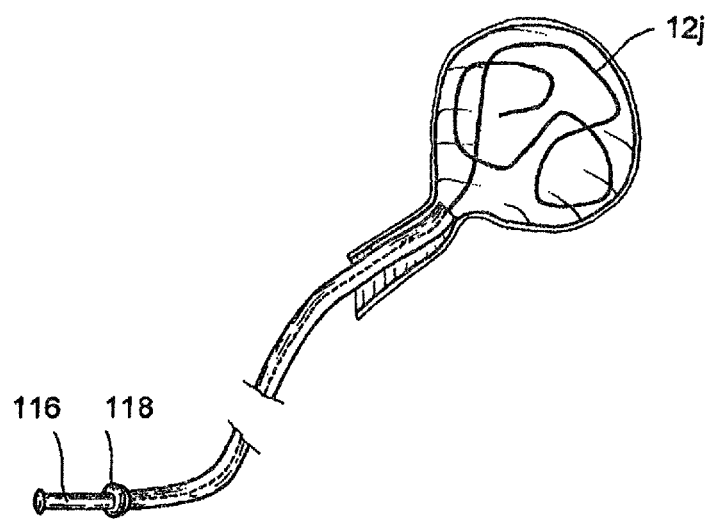
FIG. 10B is a schematic diagram showing an example of a method by which the system of FIG. 10A may be used to implant the substance eluting filament within a paranasal sinus.

FIGS. 10A and 10B show a system 110 for delivering another implantable substance delivery device which comprises a substance eluting filament 12j. This system 110 comprises the substance eluting filament 12j, a catheter 114, a pusher 116 and a connector 118. The substance eluting filament 12j is advanced into the lumen of the delivery catheter 114. The pusher 116 is advanced into the lumen of the delivery catheter 114 behind the substance eluting filament 12j and the connector 118 is connected to the proximal end of the delivery catheter 114. As shown in FIG. 10B, the delivery catheter 114 may then be advanced into the subject's body to a position where the distal end of the delivery catheter is within or near the location where the substance delivery device 12j is to be implanted (e.g., within or near the ostium of a paranasal sinus). Thereafter the pusher may be advanced in the distal direction or the pusher may be held stationary and the catheter 114 may be retracted in the proximal direction to push the substance delivery device 12j out of the end of distal end of the catheter and into the desired implantation site (e.g., paranasal sinus). The substance eluting filament may or may not be biased to a specific shape or coiled configuration. In one embodiment, the substance eluting filament 12j assumes a random coiled shape within the implant location.

Figure 11A:
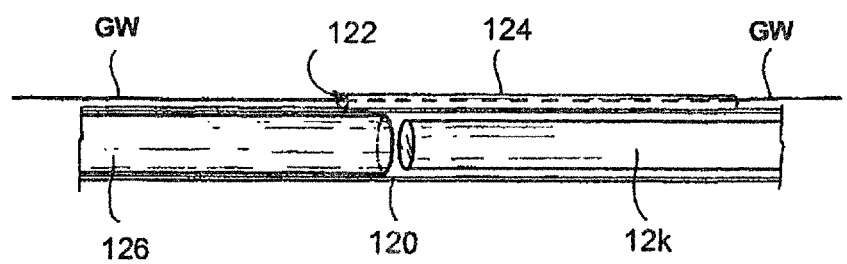
FIG. 11A is a cut-away side view of a catheter system having a second lumen that is useable for implanting an implantable substance delivery device or drug eluting filament by tracking over a previously inserted guidewire.
Figure 11B:
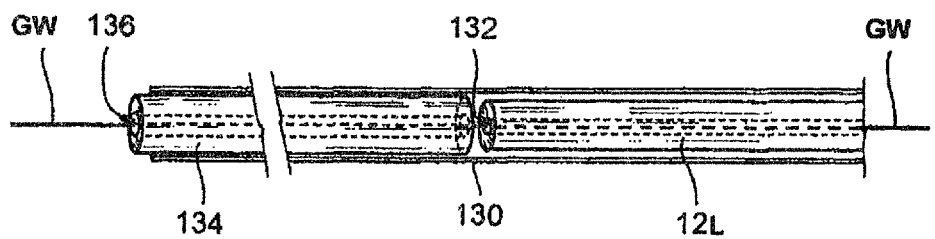
FIG. 11B is a cut-away side view of a catheter system adapted for over-the-wire delivery of an implantable substance delivery device or drug eluting filament that has a guidewire lumen extending longitudinally therethrough.

The implantable substance delivery devices 12 of this invention and/or the delivery catheter or delivery devices used to deliver such devices 12 into the body may, in some instances, be configured for over-the-wire or rapid exchange delivery. FIG. 11A shows an illustrative example of a rapid exchange embodiment of this invention and FIG. 11B shows an illustrative example of an over-the-wire embodiment. In the rapid exchange embodiment shown in FIG. 11A, the delivery catheter 120 has a first lumen within which the implantable substance delivery device 12k and elongate delivery member or pusher 126 are positioned. A side tube 124 having a second lumen 122 is located on a side of the delivery catheter 120, as shown. Thus, a guidewire GW may pass through the side lumen 122, thereby allowing the system to be advanced over a previously inserted guidewire.

FIG. 11B shows an over-the-wire embodiment comprising a delivery catheter 130 having a lumen within which the implantable substance delivery device 12l and elongate delivery member or pusher 134 are positioned. The substance delivery device 12l and elongate delivery member or pusher 134 have lumens 132 and 136 extending longitudinally therethrough. Thus, a guidewire GW may pass through the lumens 132 and 136, thereby allowing the system to be advanced over a previously inserted guidewire. Thus, it is to be understood that, wherever feasible, the substance delivery devices 12 of the present invention may have guidewire lumens or passageways extending therethrough.

Figure 12A:
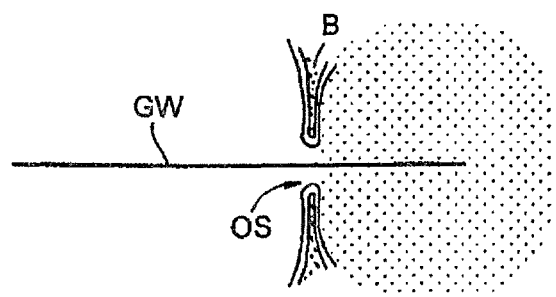
FIGS. 12A-12F are schematic diagrams showing steps in a procedure for a) access to and enlargement of the ostium of a paranasal sinus and b) implantation of an implantable substance delivery device of the present invention within the enlarged ostium and paranasal sinus.
Figure 12B:
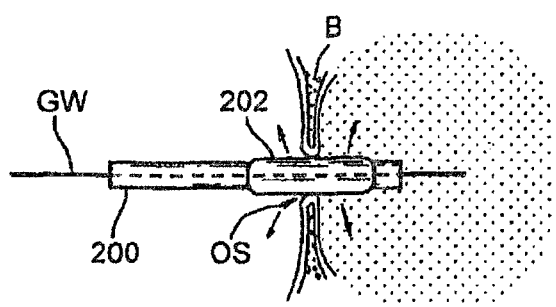
Figure 12C:
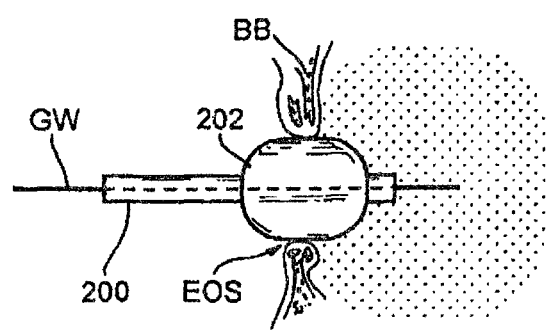
Figure 12D:
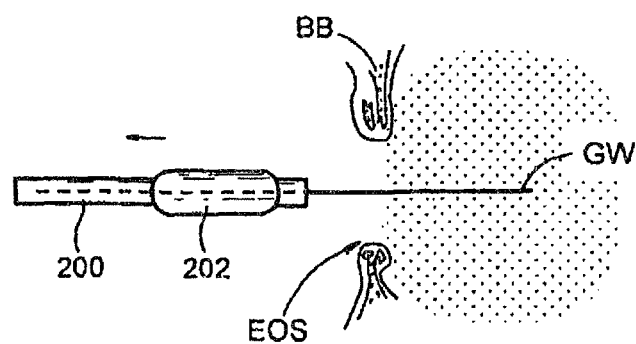
Figure 12E:
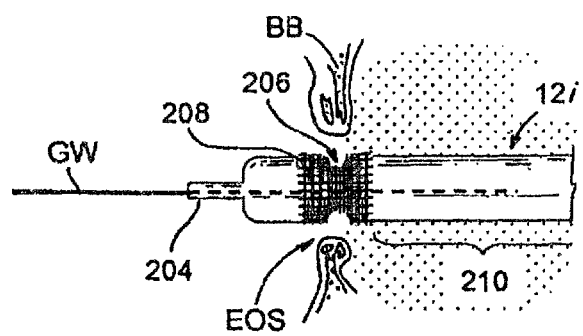
Figure 12F:
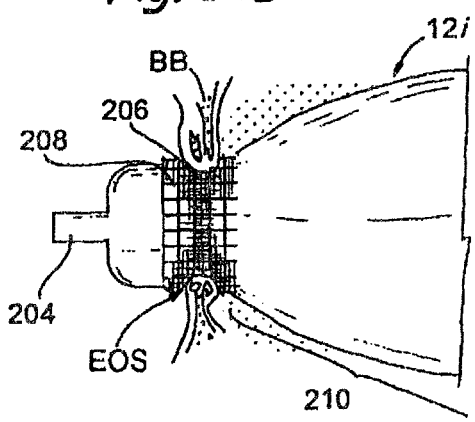

FIGS. 12A-12E show one of many possible examples of procedures that may be performed using the implantable substance delivery devices 12 of the present invention. This particular example shows a method for treating sinusitis in a human or animal subject. In this subject, the sinusitis is due at least in part to impaired drainage from the sinus as a result of an occlusion of the ostium OS that leads into the paranasal sinus. The ostium OS consists of thin bone B covered by mucosal tissue. As shown in FIG. 12A, a guidewire such as a Guidant Hi-Torque Supracore 35 Guide Wire is advanced through the ostium OS and into the paranasal sinus. As shown in FIG. 12B, a balloon catheter 200 such as the Guidant Agiltrac 0.035 Peripheral Dilatation Catheter having a balloon 202 formed of relatively strong material such as polyethylene teraphthalate is then advanced over the guidewire GW to a position where the balloon 202 is positioned within the ostium OS. Thereafter, as shown in FIG. 12B, the balloon 202 is inflated so as to dilate the ostium OS possibly breaking bone B that surrounds the ostium OS and creating an enlarged ostium EOS. Thereafter, as shown in FIG. 12C, the balloon 202 is deflated and the balloon catheter 200 is withdrawn and removed, leaving the guidewire GW in place. Thereafter, a delivery catheter of any of the type described herein is advanced over the guidewire GW and to deliver an empty implantable substance delivery device 12i of the present invention within the enlarged ostium EOS such that a portion of the device 12i extends into the sinus, as shown in FIG. 12D. In this example, the implantable substance delivery device 12i is an over the wire type device 12i having a fill tube 204, an intraostial portion 206 which includes a self-expanding frame 208 and intrasinus portion 210. As shown in FIG. 12E, after the implantable substance delivery device 12i has been positioned such that its intraostial portion is within the enlarged ostium EOS and its intrasinus portion is within the paranasal sinus, the delivery catheter and guidewire GW are removed and a quantity of the desired diagnostic or therapeutic substance (e, g, a corticosteroid, anti-inflammatory, antimicrobial, mucous modifying or mucolytic agent, or other agent or substance effective to treat sinusitis) is infused through the fill tube 204 into the device 12i. As shown in FIG. 12E, this causes the intrasinus portion 210 of the device 12i to swell or expand to an enlarged configuration that will not pass out of the enlarged ostium EOS. Also, the intraostial portion 206 and frame 208 will enlarge to an expanded configuration that exerts outward radial pressure against the enlarged ostium EOS for a period of time sufficient to allow the enlarged ostium OS and any broken bone BB therein to heal and remodel to the enlarged diameter. Also, the substance(s) that was/were introduced into the device 12i will diffuse out of the device 12 into the sinus at a desired rate, thereby providing pharmacological treatment for the infection, inflammation and/or other aspects of the sinusitis. Thereafter the device 12i may biodegrade and/or may be removed and the enlarged ostium will remain facilitating normal drainage from the sinus thereafter.

Another embodiment of the substance delivery device incorporates the addition of a micropump to one or all of the drug containing chambers. The micropump would assist in active transport of the drug across the membrane. The delivery rate of this pump could be programmed ahead of time or via remote electronics. Other methods of incorporating micromachinery or nanotechnology to enable pressure assisted transport could be added to the substance delivery device. Another example would include a semi-permeable membrane where the reservoir volume continuously shrinks as drug is eluted to maintain a certain driving pressure in the reservoir. This shrinkage could be due to elastic properties of the membrane or due to mechanically limiting and changing the space in the reservoir. These devices could be refillable.

The abovementioned embodiments may be used as spacing devices after a open surgical, laparoscopic surgical or an interventional procedure. Further, these devices may be further coated with an anti-infective agent or may be constructed of a substance which is naturally bacteriostatic to reduce the likelihood of toxic-shock syndrome or other device related infections. Such a naturally bacteriostatic material would be a biodegradable substance which, through the process of biodegradation, undergoes hydrolysis, releasing bacteriostatic substances such as hydrogen peroxide.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. All reasonable additions, deletions, modifications and alterations are to be considered equivalents of the described examples and embodiments and are to be included within the scope of the following claims.

What is claimed is:

1. A method for delivering a substance to a location within a nasal cavity, paranasal sinus or opening into a paranasal sinus, of a human or animal subject to treat a disorder, said method comprising the steps of:
    (a) obtaining or providing a device that comprises:
        (i) a reservoir that is substantially free of the substance but which may subsequently be loaded with said substance, said reservoir being sufficiently small to fit through an opening into the paranasal sinus,
        (ii) a catheter coupled with the reservoir for filling the reservoir with the substance, wherein a detachable portion of the catheter is detachable and removable after the reservoir has been filled, thereby leaving a non-detached portion of the catheter connected to the reservoir after the detachable portion of the catheter has been detached and removed,
        (iii) a closure apparatus comprising a one way valve that allows substance to be introduced through the catheter into the reservoir but prevents the substance from flowing back out of the reservoir, the detachable portion of the catheter being proximal to the closure apparatus such that the closure apparatus remains with the reservoir after the detachable portion of the catheter has been detached and removed, and
        (iv) a barrier surrounding at least part of the reservoir such that substance that has been loaded into the reservoir will pass out of the reservoir through the barrier at a known rate,
        wherein the reservoir is configured such that, when the reservoir is implanted and loaded with said substance, the reservoir will assume a configuration such that the reservoir defines at least one flow channel through which mucus or other biological fluid may drain, wherein the at least one flow channel is defined between an exterior surface of the barrier and an anatomical surface;
    (b) inserting the reservoir of the device into the nasal cavity, paranasal sinus or opening into a paranasal sinus; and
    (c) thereafter loading the substance into the reservoir, wherein the act of loading the substance into the reservoir includes urging the substance through a lumen extending longitudinally through the reservoir, wherein the lumen is contained within the reservoir.

2. A method according to claim 1, further comprising at least one substance introducing apparatus useable to introduce the substance through a fill site and into the reservoir.

3. A method according to claim 2, wherein the substance introducing apparatus comprises a syringe.

4. A method according to claim 2, wherein the device comprises a measured quantity of the substance that has been preloaded into the substance introducing apparatus.

5. A method according to claim 1, wherein the reservoir comprises a porous material which will hold a quantity of the substance, wherein the porous material is in fluid communication with the lumen.

6. A method according to claim 5, wherein the porous material is a material selected from the group of porous materials consisting of flexible polymer foams, biodegradable polymer foams, non-biodegradable polymer foams, porous PLLA, porous PLGA, porous hydrogel, polyvinyl alcohols, silicone foams, polytetrafluoroethylene, expanded polytetraflurorethylene, latex, and nylon.

7. A method according to claim 1, wherein the closure apparatus comprises a valve.

8. A method according to claim 7, wherein the valve comprises a check valve that allows fluid to be infused in a first direction into the reservoir during but thereafter prevents fluid from flowing in a second direction out of the reservoir.

9. A method according to claim 1, wherein the device has a collapsed configuration and an expanded configuration such that the device may be advanced through a passageway of the body while in its collapsed configuration and thereafter expanded to or is allowed to assume its expanded configuration.

10. A method according to claim 9, wherein introduction of the substance into the reservoir causes the device to transition from its collapsed configuration to its expanded configuration.

11. A method according to claim 1, further comprising an apparatus for moving the substance out of the reservoir and/or through the barrier.

12. A method according to claim 11, wherein the apparatus for moving the substance is selected from the group consisting of an osmotic pump, a mechanical pump, an electromechanical pump, a nanotechnology pumping mechanism and an electrical device that emits a current to drive the transport.

13. A method according to claim 1, wherein the reservoir comprises a hollow cavity in fluid communication with the lumen.

14. A method according to claim 1, wherein the reservoir comprises a hollow cavity in combination with a porous material which will hold a quantity of the substance, wherein the hollow cavity and the porous material are in fluid communication with the lumen.

15. A method according to claim 1, wherein the closure apparatus comprises a self-sealing needle port.

16. A method according to claim 1, wherein the closure apparatus comprises an applicator for applying an adhesive to a fill site to close the fill site.

17. A method according to claim 1, wherein the closure apparatus comprises a clip for closing a fill site.

18. A method according to claim 1, wherein the closure apparatus comprises a clamp for closing a fill site.

19. A method according to claim 1, wherein the closure apparatus comprises a ligature for closing a fill site.

20. A method according to claim 1, wherein the barrier has pores sized to allow passage therethrough of the substance at a rate of from 180 micrograms to 260 micrograms of triamcinolone acetonide per 24 hour period.

21. A method according to claim 1 wherein, the substance comprises triamcinolone acetonide and at least one additional agent selected from the group consisting of an imageable contrast agent, a diagnostic indicator agent, an antibiotic, an antifungal, an antiparasitic, an antimicrobial, a steroid, a vasoconstrictor, a leukotriene inhibitor, an IgE inhibitor, an anti-inflammatory, a mast cell stabilizer, an antihistamine, an imunomodulator, an SYK kinase inhibitor, a chemotherapeutic agent, an antineoplastic agent, a mucolytic agent, an agent that thins or otherwise changes the viscosity of mucous, and a substance that facilitates remodeling of soft tissue and/or bone and/or cartilage.

22. A method according to claim 1 wherein, the substance comprises triamcinolone acetonide and at least one additional steroid selected from the group consisting of beclomethasone, flunisolide, fluticasone, mometasone, aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone.

23. A method according to claim 1 wherein, the substance comprises triamcinolone acetonide and at least one antimicrobial agent selected from the group consisting of acyclovir, amantadine, aminoglycosides, amikacin, gentamicin, tobramycin, amoxicillin, amoxicillin/clavulanate, amphotericin B, ampicillin, ampicillin/sulbactarn, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscamet, ganciclovir, atifloxacin, imipenem/cilastatin, isoniazid, itraconazole, ketoconazole, metronidazole, nafcillin, nafcillin, nystatin, penicillin, penicillin G, pentamidine, piperacillin/tazobactam, rifampin, quinupristin-dalfopristin, ticarcillin/clavulanate, trimethoprim/sulfamethoxazole, valacyclovir, vancomycin, mafenide, silver sulfadiazine, mupirocin, nystatin, triamcinolone/nystatin, clotrimazole/betamethasone, clotrimazole, ketoconazole, butoconazole, miconazole, tioconazole, detergent-like chemicals that disrupt or disable microbes, nonoxynol-9, octoxynol-9, benzalkonium chloride, menfegol, and N-docasanol, chemicals that block microbial attachment to target cells, chemical that inhibits entry of infectious pathogens into cells, sulphated polymers, sulponated polymers, carrageenan, antiretroviral agents, PMPA gel, antibodies, genetically engineered or naturally occurring antibodies that combat pathogens, plantibodies, agents which change the condition of the tissue to make it hostile to the microbes, agents which alter mucosal pH, buffer gel, acidform and non-pathogenic microbes that kill or inhibit the growth of pathogenic microbes.

24. A method according to claim 1, wherein the device is at least partially biodegradable.

25. A method according to claim 1, further comprising a graspable member extending from the device to facilitate grasping and removal of the device.

26. A method according to claim 1, wherein the device has a substantially rectangular cross-sectional configuration.

27. A method according to claim 1, wherein the reservoir is further configured such that, when the reservoir is implanted and loaded with said substance, the reservoir will assume a configuration that an exterior surface of the reservoir defines at least one projection configured to contact an interior surface of the paranasal sinus.

28. A method according to claim 1, wherein the device has an intraosteal portion that is configured to be implanted within the ostium of a paranasal sinus and an intrasinus portion that is intended to extend into the paranasal sinus.

29. A method for delivering a substance to a location within a nasal cavity, paranasal sinus or opening into a paranasal sinus, of a human or animal subject to treat sinusitis, said method comprising the steps of:
(a) obtaining or providing a system that comprises:
(i) a substance delivery device, comprising:
(A) a reservoir that is substantially free of the substance but which may subsequently be loaded with said substance, said reservoir being sufficiently small to fit through an opening into the paranasal sinus, wherein the reservoir comprises a porous material disposed about a porous lumen extending longitudinally through the reservoir, and
(B) a barrier surrounding at least part of the reservoir such that the barrier substantially encompasses the porous material and at least part of the porous lumen and such that substance that has been loaded into the reservoir will pass out of the reservoir through the barrier at a known rate,
wherein the reservoir is configured such that, when the reservoir is implanted and loaded with said substance, the reservoir will assume a configuration such that the reservoir defines at least one flow channel through which mucus or other biological fluid may drain, wherein the at least one flow channel is defined between an exterior surface of the barrier and an anatomical surface,
(ii) a delivery catheter system comprising a catheter that is coupled with the reservoir for filling the reservoir with the substance, wherein a detachable portion of the catheter is detachable and removable after the reservoir has been filled, thereby leaving a non-detached portion of the catheter connected to the reservoir after the detachable portion of the catheter has been detached and removed, and
(iii) a closure apparatus comprising a one way valve that allows substance to be introduced through the catheter into the reservoir but prevents the substance from flowing back out of the reservoir, the detachable portion of the catheter being proximal to the closure apparatus such that the closure apparatus remains with the reservoir after the detachable portion of the catheter has been detached and removed;
(b) using the delivery catheter system to deliver the substance delivery device to a position where the reservoir is positioned in the paranasal sinus; and
(c) loading the substance into the reservoir, wherein the act of loading the substance into the reservoir comprises urging the substance through a-the barrier and into the reservoir.

30. A method according to claim 29, wherein the delivery catheter system comprises:
(A) a catheter that has a lumen and a distal opening, said substance delivery device being positioned within the lumen of the catheter, and (B) a member positioned within the lumen of the catheter proximal to the implantable substance delivery device;

at least one of said catheter and said member being moveable relative to the other so as to expel the implantable substance delivery device out of the distal opening of the catheter.

31. A method according to claim 30, wherein the substance delivery device and the member positioned within the lumen of the catheter have guide wire passageways extending therethrough so as to allow the system to be advanced over a guide wire.

32. A method according to claim 30, wherein the catheter further comprises a second lumen sized to permit a guidewire to pass therethrough, said second lumen being useable to allow the system to be tracked in a previously inserted guidewire.

33. A method for delivering a substance to a location within a nasal cavity, paranasal sinus or opening into a paranasal sinus, of a human or animal subject to treat a disorder, said method comprising the steps of:
   (a) obtaining or providing a device that comprises:
      (i) a porous lumen having a distal end and a proximal end,
      (ii) a porous barrier having a distal end and a proximal end, wherein the distal end of the barrier is coupled to the distal end of the lumen, wherein the proximal end of the barrier is coupled to an exterior surface of the lumen at a position distally of the proximal end of the lumen,
      (iii) a reservoir defined between an exterior surface of the lumen and an interior surface of the barrier and between the proximal end of the barrier and the distal end of the barrier such that the lumen extends the length of the reservoir, wherein the reservoir is substantially free of the substance but may subsequently be loaded with the substance, the reservoir being sufficiently small to fit through an opening into the paranasal sinus,
         wherein the reservoir is configured such that, when the reservoir is implanted and loaded with said substance, the reservoir will assume a configuration such that the reservoir defines at least one flow channel through which mucus or other biological fluid may drain, wherein the at least one flow channel is defined between an exterior surface of the barrier and an anatomical surface,
      (iv) a catheter configured to provide the substance to the reservoir, and
      (v) a closure apparatus coupled to the proximal end of the lumen, wherein the closure apparatus is selectively coupleable to the catheter, wherein the closure apparatus is configured to allow the substance to be introduced through the catheter into the reservoir but prevents the substance from flowing back out of the reservoir,
   (b) inserting the reservoir of the device into the nasal cavity, paranasal sinus or opening into a paranasal sinus; and
   (c) thereafter loading the substance into the reservoir, wherein the act of loading the substance into the reservoir includes urging the substance through the lumen.

\* \* \* \* \*